US007619072B2

(12) United States Patent
Jones

(10) Patent No.: US 7,619,072 B2
(45) Date of Patent: Nov. 17, 2009

(54) PURIFICATION METHOD FOR RECOMBINANT GLUCOSE BINDING PROTEIN

(75) Inventor: David Hugh Jones, Swansea (GB)

(73) Assignee: UWS Ventures Limited, Swansea (GB)

(*) Notice: Subject to any disclaimer, the term of this patent is extended or adjusted under 35 U.S.C. 154(b) by 139 days.

(21) Appl. No.: 10/595,954

(22) PCT Filed: Nov. 19, 2004

(86) PCT No.: PCT/GB2004/004907

§ 371 (c)(1),
(2), (4) Date: May 22, 2006

(87) PCT Pub. No.: WO2005/051987

PCT Pub. Date: Jun. 9, 2005

(65) Prior Publication Data

US 2007/0142624 A1 Jun. 21, 2007

(30) Foreign Application Priority Data

Nov. 21, 2003 (GB) ................................. 0327179.8

(51) Int. Cl.
*C07K 16/00* (2006.01)
*A23J 1/00* (2006.01)
(52) U.S. Cl. ...................................... 530/396; 530/412
(58) Field of Classification Search ................. 530/396, 530/412, 413, 416
See application file for complete search history.

(56) References Cited

U.S. PATENT DOCUMENTS

| | | | |
|---|---|---|---|
| 6,232,130 | B1 | 5/2001 | Wolf |
| 2005/0095174 | A1 | 5/2005 | Wolf |

FOREIGN PATENT DOCUMENTS

| | | | |
|---|---|---|---|
| DE | 19501159 | A1 | 7/1996 |
| DE | 19714087 | A1 | 10/1998 |
| WO | 9109312 | A1 | 6/1991 |
| WO | 9400602 | A1 | 1/1994 |
| WO | 98/55869 | A | 12/1998 |
| WO | 9855869 | A1 | 12/1998 |
| WO | 00/16099 | A | 3/2000 |
| WO | 0016099 | A1 | 3/2000 |
| WO | 2005044100 | A1 | 5/2005 |

OTHER PUBLICATIONS

Edelman et al, Isolation and Proteolytic Cleavage of the Intact Subunit of Concanavalin, Biochemistry, vol. 11, No. 17, 1972, pp. 3233-3239.
Agravval et al, Concanavalin A, The Jack Bean (*Canavalia ensiformis*) Phytohemagglutinin, Methods in Enzymology, vol. 28, Complex Carbohydrates Part B, Victor Ginsburg (ed.), pp. 313-318, 1972, Academic Press, New York, NY.
Agrawal et al, Protein-Carbohydrate Interaction: VI. Isolation of Concanavalin A By Specific Adsorption on Cross-Linked Dextran Gels, Biochim Biophys Acta, 1967, pp. 262-271, vol. 147, Issue 2.
Becker et al, The Molecular Structure of Concanavalin A, 1976, Concanavalin A as a Tool, Bittiger and Schnebli (ed.), Chapter 3, pp. 33-54.
Beutler, Starch, Methods of Enzymatic Analysis, 1984, Third Edition, vol. VI, Metabolites 1: Carbohydrates, Bergmeyer (ed.), pp. 2-10.
Beyer et al, Recording of Subcutaneous Glucose Dynamics By a Viscometric Affinity Sensor, Diabetologia, 2001, pp. 416-423, vol. 44, Issue 4.
Bowden et al, Structure and Morphology of Protein Inclusion Bodies in *Escherichia coli*, Biotechnology, vol. 9, Aug. 1991, pp. 725-730.
Bowles et al, Traffic and Assembly of concanavalin A, Trends in Biochemistry and Science, Feb. 1988, vol. 13, Issue 2, pp. 60-64, Elsevier Publications Cambridge.
Eggins, Biosensors: An Introduction, 1996, pp. 92-97 & 140-143.
Eggins, Chemical Sensors and Biosensors, 2002, pp. 178-182.
Jones, Folding, Activation and Protein Splicing of Recombinant concanavalin A Precursors: An Exceptional Protein to Prove Some Rules, Chapter 20, pp. 70-73, Perspectives on Protein Engineering & Complementary Technologies, Epton & Geisow (ed.), 1995.
Dawes, Storage Polymers in Prokaryotes, pp. 81-122, Prokaryotic Structure and Function: A New Perspective, Dow, Coles and Mohan (ed.), 1992, Cambridge University Press, Cambridge.
Dawson et al, Data for Biochemical Research, pp. 288-289, 404-405, 417-425, 439-440 & 541-542, Third Edition, Oxford University Press, New York, 1986.
Dubois et al, Colorimetric Method for Determination of Sugars and Related Substances, Analytical Chemistry, vol. 28, No. 3, Mar. 1956, pp. 350-356, American Chemical Society.
Georgiou et al, Isolating Inclusion Bodies From Bacteria, pp. 48-58. Chapter 3, Amyloid, Prions and Other Protein Aggregates, Wetzel (ed.), Methods in Enzymology, vol. 309, 1999, Academic Press.
Goldstein et al, Agar Gel-Diffusion Studies on the Interaction on concanavalin A, a Lectin Isolated from Jack Bean, with Polysaccharides, pp. 407-414, Archives of Biochemistry and Biophysics, vol. 111, Aug. 1965, Elsevier.
Goldstein et al, Isolation and Chemical Properties of Lectins, pp. 148-247, The Lectins: Properties, Functions and Applications in Biology and Medicine, 1986, Liener, Sharon & Goldstein (ed.), Academic Press.
Goldstein et al, Isolation, Physicochemical Characterization, and Carbohydrate-Binding Specificity of Lectins, pp. 32-137, Chapter 2, The Lectins: Properties, Functions and Applications in Biology and Medicine, 1986, Liener, Sharon & Goldstein (ed.), Academic Press.

(Continued)

*Primary Examiner*—Suzanne M. Noakes
(74) *Attorney, Agent, or Firm*—Brooks Kushman P.C.

(57) ABSTRACT

The present invention relates to a method for purifying a recombinant glucose binding protein, in particular the lectin Concanavalin A (Con A). The method specifically utilizes a buffer in which impurities, such as glycogen and other substances are soluble, but in which the protein remains insoluble. The use of such buffers, and the purified proteins are also described.

20 Claims, 9 Drawing Sheets

OTHER PUBLICATIONS

Hengge-Aronis et al, Identification and Molecular Analysis of glgS, a Novel Growth-Phase-Regulated and rpoS-Dependant Gene Involved in Glycogen Synthesis in *Escherichia coli*, pp. 1877-1886, Molecular Microbiology, Jul. 1992, vol. 6, Issue 16.

Hodge et al, Determination of Reducing Sugars and Carbohydrates, pp. 380-393, Methods in Carbohydrate Chemistry, vol. 1: Analysis and Preparation of Sugars, Whistler and Wolfrom (ed.), 1962, Academic Press, New York.

Hoedemaeker et al, Destabilization of Pea Lectin by Substitution of a Single Amino Acid in a Surface Loop, pp. 1039-1046, Plant Molecular Biology, vol. 22, No. 6, Sep. 1993, Kluwer Academic Publishers, Belgium.

Horstmann et al, Isolation, Characterization and Subunit Structure of a Phytohemagglutinin from Seeds of Vicia faba L., pp. 311-321, Biochem. Physiol. Pflanzen 173, 1978.

Min et al, Stability and Detection of Recombinant Pre-Pro-concanavalin A after Cytoplasmic Expression in *Escherichia coli*, pp. 315-318, FEBS Letters, vol. 301, No. 3, 1992.

Min et al, Non-Glycosylated Recombinant pro-concanavalin A is Active Wthout Polypeptide Cleavage, pp. 1303-1307, The EMBO Journal, vol. 11, No. 4, 1992, Oxford University Press.

Dincturk et al, Recombinant pre-pro-concanavalin A (Jack Bean) is Stable But of Low Solubility, pp. 635-640, Journal of Biosciences, vol. 26, No. 5, Dec. 1995, Nanjundiah (ed.).

Schultz, Design of Fibre-Optic Biosensors Based on Bioreceptors, pp. 639-654, Biosensors: Fundamentals and Applications, Chapter 32, Turner, Karube and Wilson (ed.), 1987, Oxford University Press, New York.

Schultz et al, Affinity Sensor: A New Technique for Developing Implantable Sensors for Glucose and Other Metabolites, pp. 245-253, Diabetes Care, vol. 5, No. 3, May-Jun. 1982.

Kennedy et al, An Assessment of the Fractionation of Carbohydrates on concanavalin A-Sepharose 4B by Affinity Chromatography, pp. 2041-2046, Journal of the Chemical Society[Perkin 1], vol. 19, 1973.

Keppler et al, Glycogen, pp. 11-18, Methods of Enzymatic Analysis, vol. VI, Metabolites 1: Carbohydrates, Third Edition, 1984, Bergmeyer (ed.), Weinheim, Deerfield Beach, Florida.

Laemmli, Cleavage of Structural Proteins During the Assembly of the Head of Bacteriophage 14, pp. 680-685, Nature, vol. 227, No. 5259, Aug. 1970.

Leiner, Isolation and Properties of concanavalin A, pp. 17-31, Concanavalin A as a Tool, Chapter 2, Bittiger and Schnebli (ed.), 1976, John Wiley & Sons.

Lloyd, Affinity Chromatography on Immobilized concanavalin A, pp. 323-331, Concanavalin A as a Tool, Chapter 36, Bittiger and Schnebli (ed.), 1976, John Wiley & Sons.

Marston, The Purification of Eukaryotic Polypeptides Synthesized in *Escherichia coli*, pp. 1-12, Biochemical Journal, vol. 240, 1986, Great Britain.

Matsuura et al, A Simple and Effective Solvent System for Elution of Gonadotropins from concanavalin A Affinity Chromatography, pp. 402-410, Analytical Biochemistry, vol. 106, 1980.

McKenkie et al, The Molecular Weight and Stability of concanavalin A, pp. 283-293, Biochimica et Biophysica Acta, vol. 263, 1972.

Min et al, In Vitro Splicing of concanavalin A is Catalyzed by Asparaginyl Endopeptidase, pp. 502-504, Nature Structural Biology, vol. 1, No. 8, Aug. 1994.

Mitraki et al, Protein Folding Intermediates and Inclusion Body Formation, pp. 690-697, Bio/Technology, vol. 7, Jul. 1989.

Neidhardt, Chemical Composition of *Escherichia coli*, pp. 3-6, *Escherichia coli* and *Salmonella typhimurium*: Cellular and Molecular Biology, vol. 1, 1987, American Society for Microbiology, Washington, D.C.

West et al, Lectin Affinity Chromatography, pp. 177-185, Methods in Molecular Biology, vol. 50: Protein Purification Protocols, 1996, Walker (ed.), Humana Press, Totowa, New Jersey.

Northcote, Qualitative, Quantitative and Preparative Electrophoretic Separations of Neutral Polysaccharides, pp. 49-53, Methods in Carbohydrate Chemistry, vol. V: General Polysaccharides, 1965, Academic Press.

Pickup et al, In Vivo Glucose Sensing for Diabetes Management Progress towards Non-Invasive Monitoring, pp. 1-4, BMJ, vol. 319, 1999.

Prasthofer et al, Design, Expression and Crystallization of Recombinant Lectin from the Garden Pea (*Pisum sativum*), pp. 6793-6796, The Journal of Biological Chemistry, vol. 264, No. 12, 1989, The American Society for Biochemistry and Molecular Biology, Inc.

Preiss et al, Physiology, Biochemistry and Genetics of Bacterial Glycogen Synthesis, pp. 183-238, Advances in Microbial Physiology, vol. 30, 1989, Rose and Tempest (ed.), Academic Press.

Sambrook et al, Molecular Cloning: A Laboratory Manual, pp. 6.6-6.7, Second Edition, 1989, Cold Spring Harbor Laboratory Press.

Stryer, Biochemistry, Chapter 23: Glycogen Metabolism, p. 581, 1995, W.H. Freeman and Company, New York.

Stubbs et al, Production of Pea Lectin in *Escherichia coli*, pp. 6141-6144, The Journal of Biological Chemistry, vol. 261, No. 14, May 1986, The American Society of Biological Chemists, Inc.

Sumner et al, The Identification of the Hemagglutinin of the Jack Bean with concanavalin A, pp. 227-237, Journal of Bactebiology, vol. 32, No. 2, 1936.

Svensson et al, The Effect of Borate on Polysaccharide-Protein and Antigen-Antibody Reactions and Its Use for the Purification and Fractionation of Crossreacting Antibodies, pp. 415-422, Immunochemistry, vol. 7, 1970, Pergamon Press, Great Britain.

Thatcher et al, Protein Folding in Biotechnology, pp. 229-261, Mechanisms of Protein Folding, Pain (ed.), 1994, Oxford University Press, New York.

van Eijsden et al, Mutational Analysis of Pea Lectin. Substitution of Asn125 for Asp in the Monosaccharide-Binding Site Eliminates Mannose/Glucose-Binding Activity, pp. 1049-1058, Plant Molecular Biology, vol. 20, 1992, Kluwer Academic Publishers, Belgium.

Min W et al, "Stability and Detection of Recombinant Pre-Pro-Concanavalin A After Cytoplasmic Expression in *Escherichia coli*" 1992, FEBS Letters, vol. 301, nr. 3, pp. 315-318, ISSN: 0014-5793.

Dincturk H Benan et al, "Recombinant Pre-Pro-Concanavalin A (Jack Bean) is Stable But of Low Solubility" Dec. 2001, Journal of Biosciences (Bangalore), vol. 26, nr. 5, pp. 635-640, ISSN: 0250-5991.

Min W et al, "Non-Glycosylated Recombinant Pro-Concanavalin A is Active Without Polypeptide Cleavage" EMBO (European Molecular Biology Organization) Journal, vol. 11, No. 4, 1992, pp. 1303-1307, ISSN: 0261-4189.

PURIFICATION METHOD FOR RECOMBINANT GLUCOSE BINDING PROTEIN

CROSS-REFERENCED TO RELATED APPLICATION

This application is the U.S. national phase of PCT Appln. No. PCT/GB2004/04907 filed Nov. 19, 2004 which claims priority to Great Britain application GB 0327179.8 filed Nov. 21, 2003.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

SUMMARY

The present invention relates to a method for obtaining a recombinant glucose binding protein, in particular the lectin Concanavalin A (Con A). The method specifically utilizes a buffer in which impurities, such as glycogen and other substances are soluble, but in which the protein remains soluble. The use of such buffers, and the purified proteins are also described.

DETAILED DESCRIPTION OF EMBODIMENTS OF THE PRESENT INVENTION

Figure 1:
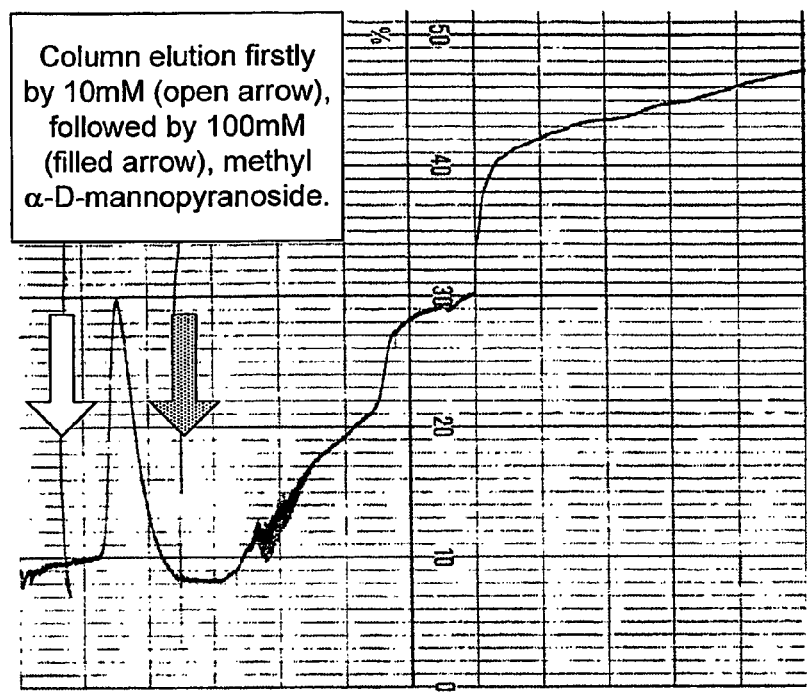
FIG. 1 depicts dextran affinity chromatography elution profile for recombinant mature Con A refolded from the bacterial cell fraction insoluble in MOPS-metals buffer.

The present invention relates to a method for purifying a recombinant glucose binding protein, in particular the lectin Concanavalin A (Con A). The method specifically utilises a buffer in which impurities, such as glycogen and other substances are soluble, but in which the protein remains insoluble. The use of such buffers, and the purified proteins are also described.

Con A is the best-characterised member of a large family of homologous carbohydrate-recognising proteins abundant in the seeds of leguminous plants [1]. Con A was the first of the legume lectins to be isolated [2] and is specific primarily for mannose, glucose and polysaccharides carrying these as α-linked non-reducing terminal sugars [1]. The saccharide specificity of Con A (found in the Jackbean *Canavalia ensiformis*) is similar to that of the closely related lectins from pea (*Pisum sativum*), lentil (*Lens culinaris*) and broad bean (*Vicia faba*). In addition to these members of the "Glucose/Mannose Group", there are many other lectins from leguminous and other sources with very different specificities [1].

The natural plant source is rich in Con A (about 10% by weight of the Jackbean seed) and a saline extraction process produces crystallisable lectin [2]. However, the well-established method of purification is by affinity chromatography utilising the bio-specificity of this protein. Con A was the first lectin to be isolated by this technique. It binds readily to a cross-linked dextran gel (primarily an α-(1→6) linked glucose polymer in beaded form, e.g. Sephadex G-75™ and may be specifically eluted with a cognate monosaccharide for example, glucose, mannose or derivatives [3, 4]. This straightforward affinity purification methodology is widely used to produce commercially available native Con A and related lectins from their natural sources (e.g. Sigma-Aldrich Co., Poole, UK: Biochemicals and Reagents Catalogue 2002-03).

At neutral pH, Con A is a tetramer of non-glycosylated subunits each of a molecular weight of 25,600 Da, but preparations of native Con A contain variable amounts of two smaller polypeptide fragments in addition to these intact subunits [1]. These fragments are the result of incomplete post-translational processing involving proteolytic cleavages, re-ligation and circular sequence permutation of precursor proteins during the complex biosynthesis of this lectin in the developing seed (summarised in [5] and [6]). The mature form of Con A is circularly permutated with respect to legume lectins. However, the amino acid sequence derived from the cDNA for the Con A precursor (pro-Con A) has direct, and not circular homology with other legume lectins. Therefore, a post-translational transposition and ligation (at mature protein residues 118 and 119) of two polypeptides must occur. Furthermore, the pro-Con A made in the plant is glycosylated, and unable to bind to cross-linked dextran. The oligosaccharide is removed prior to the proteolytic cleavages during post-translational processing in the plant.

It is desirable to express the various forms of this protein from cloned DNA sequences. This would allow the processing intermediates which are difficult to isolate from the plant to be obtained, in order to study the mechanism of their biosynthesis. It would also enable the structure and/or function of any form to be manipulated by protein engineering (site-directed mutagenesis). In addition a secure and (in principle) unlimited and highly consistent supply of any form of the protein would be produced for any purpose for which this might be required.

For many current uses the natural and commercially available Jackbean-derived lectin may be adequate. However, recombinant mature Con A, expressed directly in bacteria from re-ordered segments of precursor DNA, has not undergone the plant biosynthetic process and hence is uncontaminated with the smaller polypeptide fragments mentioned earlier. This recombinant protein might thus be superior to the native protein for some applications.

Natural plant-derived Con A has received considerable attention as a suitable bio-receptor molecule for the determination of glucose concentrations in blood and tissue-fluid during management of diabetes mellitus [7], [8]. Such biosensors all follow a common principle whereby glucose concentration is indirectly determined in a competitive binding method. The bio-receptor (Con A) binds to an analyte-analogue (some form of glucose derivative, often a polymer of glucose or glucose covalently attached to a carrier molecule) and this bio-specific interaction is disrupted by free analyte (glucose) molecules. The proportion of the bio-receptor bound to either free glucose or to the analyte-analogue is a measure of glucose concentration according to the competing equilibria present. A signal is generated by various means to assess the proportion of Con A binding to glucose-analogue and hence quantify the free glucose concentration [7], [8].

One approach to generating a signal relies on glucose-dependent changes in the viscosity of a mixture of plant-derived Con A and dextran (as the analyte-analogue) [9], [10], [11]. This glucose-sensitive liquid is enclosed in capillaries tipped by a microdialysis probe implanted into the subcutis and continuous viscometric sensing is achieved via pressure transducers [11].

Signal generation by fluorescence-based techniques has received much attention for a considerable period of time [12] with either native Con A or an analyte-analogue (e.g. dextran) being fluorescently-labelled [13]. In further developments, each of these components carries different labels so that a fluorophore donor and acceptor relationship enables Fluorescence Resonance Energy Transfer (FRET) as a signal generation technology e.g. see FIG. 3 of ref. [14] where near-infra red fluorescent dyes are also used. In one case using natural plant Con A, the analyte-analogue is glucose covalently attached to a carrier protein (neo-glycosylated serum albumin) and the sensor is implantable sub-cutaneously to permit non-invasive in vivo monitoring of glucose in body fluids [15], [16]. This technology has been developed to include reduced valency plant-derived Con A [17], [18] and possibly some form of reduced valency Con A which might somehow be made by recombinant means [19].

The first forms of recombinant Con A expressed corresponded to precursors present in developing seeds: pre-pro-Con A [20] and pro-Con A (non-glycosylated) [5]. Later forms included subunit fragments (A-chain and B-chain) [21], mature lectin [6] and various further derivatives of these proteins. Active recombinant forms of Con A following expression in bacteria (*Escherichia coli*) have been purified utilising the process described by Min et al. [5]. This procedure is summarised below from the point of harvesting of bacterial cells that had earlier been induced to express and accumulate recombinant lectin in liquid culture.

Cells were collected and resuspended in 50 ml MOPS-metals buffer (20 mM MOPS [3-(N-morpholino)propanesulphonic acid] pH 7.0, 1 mM $CaCl_2$, 1 mM $MnCl_2$, 1 M NaCl) and lysed by sonication (3×30 s) on ice. The lysate was placed on ice for 1 h followed by centrifugation at 27 000×g for 30 min at 4° C. The supernatant was used as a soluble extract and subjected directly to dextran affinity chromatography (see below). However, the major portion of recombinant lectin was found in the pelleted debris after cell lysis and this insoluble material was refolded as follows.

The pelleted cell debris was resuspended in 2 ml denaturant (7 M guanidine hydrochloride in MOPS-metals buffer) and placed on a rotator overnight at 4° C. Following centrifugation (27 000 g for 30 min at 4° C.) supernatant was mixed for 30 min with 0.5 ml DEAE-Sephacel (Pharmacia) equilibrated in the same denaturant [22], then centrifuged as before. The DEAE-Sephacel pellet was discarded and the supernatant diluted at least 30-fold with MOPS-metals buffer, kept for 1 h at room temperature, then centrifuged as before.

Dextran affinity chromatography [1]: either cell lysate containing de novo soluble product or product solubilized from pelleted cell debris by denaturant and refolded (as above), was passed down a column (10×65 mm bed) of Sephadex G-75 (Pharmacia, dry particle size 40-120 μm). A new column of affinity matrix was used for each separation to avoid cross-contamination. The sample was loaded at a low flow rate (0.05-0.1 ml/min) and the column washed (0.5-1 ml/min) to base line $A_{280}$ with MOPS-metals buffer, then eluted (0.2 ml/min) with 1 or 10 mM methyl α-D-mannopyranoside in the same buffer and any $A_{280}$ peak collected.

With this method there are practical difficulties in handling sticky pellets of crude insoluble material and other problems regarding its reproducibility and the quality and quantity of the recombinant protein produced. Stained SDS-PAGE (Sodium Dodecyl Sulphate—Poly Acrylamide Gel Electrophoresis) indicates that usually one protein species is isolated and Western blotting and N-terminal protein sequencing identify this as a form of Con A [5]. However, the yield of recombinant product is low and unreliable. The purity is called into question by broadening of the monosaccharide-elution $A_{280}$ profiles during affinity chromatography (FIG. 1), relative to the sharp profiles indicating homogeneous binding which are observed with authentic native Con A samples. Sometimes chromatography columns can become blocked by formation of some insoluble material or eluted fractions may show turbidity. Furthermore, the UV absorption spectrum of the material obtained (FIG. 2) indicates the presence of nucleic acid-derived contaminants resulting in over-estimation of the protein concentration relative to that expected from N-terminal sequencing results [5].

The isolation procedure was based on earlier methods [22] for recombinant pea lectin, and was also used by other workers on this protein [23], [24], [25]. Native pea lectin has similar properties to Con A and it would seem probable that similar problems might be encountered with this procedure as used with recombinant pea lectin. There appears to be no evidence that such possible inconsistencies have been eliminated in working with proteins related to Con A. It therefore appears that there are some further possible factors which compromise the quality and quantity of recombinant products obtainable.

The problems and inconsistencies given above are not simply the result of low expression levels of recombinant product, since changing the expression plasmids to newer higher level vectors did not overcome the difficulties of purification but rather highlighted them. The cellular location of the expressed product is periplasmic [5], although similar difficulties are also expected for product accumulating in the bacterial cytoplasm. During the isolation procedure outlined above, other molecules/macromolecules present in the bacterial cell are released and carried through the process where they can interfere with the purification of active soluble forms of Con A and contaminate and form complexes with the preparations obtained.

Evidence for the presence of interfering materials was obtained by adding pure soluble (commercially-available) native Con A to extracts of bacterial cells not capable of expressing recombinant lectin. In these "spiking" experiments, precipitates formed and poor recovery of the added protein was obtained. On addition of competing monosaccharide (methyl α-D-mannopyranoside at a concentration of 10 mM), these precipitates re-dissolved: showing that their formation was dependent on the binding activity of Con A. The interfering materials could not be removed from Con A by dialysis, including dialysis in the presence of competing monosaccharide, consistent with macromolecular properties for some of the components.

The applicant has found that one of the interfering substances is glycogen synthesized in the bacterial cell, and that this can form a complex with active Con A which may trap other molecules such as nucleic acid derivatives and other substances. The presence of glycogen would reduce the quantity of recombinant lectin isolated and compromise its quality by contaminants. However, materials other than glycogen may also cause purification problems.

Glycogen is a storage polymer of glucose units mostly linked α-(1→4) with frequent α-(1→6) branching, thus carrying multiple terminal non-reducing α-glucose units [26] which can serve as receptors for Con A through the "chain-end mechanism" of interaction [1]. Sumner and Howell [2] first showed that native Con A could precipitate glycogen and Goldstein and So [27] demonstrated that it formed precipitates with a wide range of polysaccharides including glycogen from *Escherichia coli*. This bacterium contains at least as much glycogen (2.5% dry weight) as it does peptidoglycan in its cell wall [28]. The accumulation of glycogen is increased in carbon-rich media and is inversely related to growth rate [29], [30]. The molecular weight of glycogen from *E. coli* ranges from $10^6$-$10^8$ [28], [30]: well above the cut-off of dialysis membranes.

The high starch content of the Jackbean seed does not seem to cause similar problems in the isolation of native Con A from its natural source. This is at first surprising, since the basic chemical structure of starch and glycogen is very similar. However, in plant cells starch grains are formed which can retain the polysaccharide in an insoluble form, whereas in the bacterial cell glycogen is soluble in the cytoplasm and would be released on cell breakage. It was confirmed by experiment that Jackbean seed meal did not release soluble starch into MOPS-metals buffer, but that the insoluble material tested positive for starch with iodine. Whereas some Con A is probably lost by adsorption to starch grains during extraction from its natural source so decreasing the quantity obtained, this insoluble material would be removed by centrifugation so that appreciable amounts of starch would not be carried through the process to affect the quality of the preparation. Therefore, the problem of glycogen forming a complex with recombinant Con A is a consequence of the use of a bacterial cell as expression host.

It is desirable to produce pure soluble homogeneous active recombinant Con A, but problems arise whenever active lectin contacts some cell components, of which glycogen is a major though not the sole interfering molecule. Although there are a number of potential methods by which the product might be separated from cell components, such as making soluble extracts of periplasm only i.e. without releasing cytoplasmic contents, acetic acid extraction of Con A from cell debris, extraction in the presence of competing monosaccharide, and enzyme digestion of glycogen then dialysis, these have all been unsuccessful.

Figure 2:
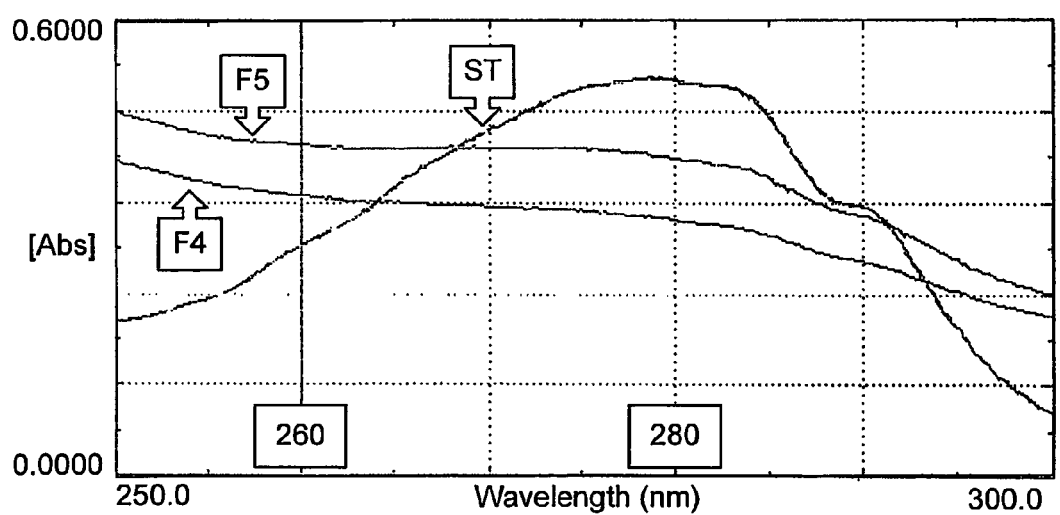
FIG. 2 depicts UV spectral wavelength scan after affinity chromatography of recombinant mature Con A (refolded from the bacterial cell fraction insoluble in MOPS-metals buffer)

Expression experiments in mutant *E. coli* strains [31] which were defective in glycogen synthesis have also been carried out. When preparations were made as described earlier [5], broadened affinity elution peaks were still obtained (FIG. 3)—though different in profile than those from glycogen-containing host cells (FIG. 1). Although the UV spectral scan was improved (FIG. 4) compared to glycogen-containing cells (FIG. 2), the purity was still not comparable to native plant Con A (FIG. 2). Besides nucleic acid derivatives, other possible contaminating cell components might include lipopolysaccharides, especially from *E. coli* B-derived strains since these are possible Con A receptors [32].

The problem could be solved in principle if the interfering substances could be solubilised and removed, whilst retaining the accumulated recombinant lectin as an insoluble form, which could later be dissolved in denaturant, refolded and recovered by affinity chromatography. The major portion of recombinant lectin was generally present in the fraction insoluble in MOPS-metals buffer as used in Min et al. [5], but this buffer did not appear to successfully remove the interfering substances (FIGS. 1-4). Therefore there is a need for solution formulations and a washing regime that successfully accomplishes the removal of interfering molecules with minimal losses of desired protein product.

The possible nature of the insoluble Con A protein contained in this fraction [5] must be considered when designing such solution formulations. During high level expression of proteins in heterologous environments, especially bacterial hosts, it is not unusual for dense aggregates of inactive recombinant protein to form. It is generally accepted that these aggregates or "inclusion bodies" are the result of aggregation of partly-folded or misfolded protein chains [33] produced at high concentrations in an environment which is not conducive to proper folding. Most examples of such insoluble misfolded aggregates have been produced in the bacterial cytoplasm, but they are also known to form when the product is secreted to the periplasm [34]. Periplasmic inclusion bodies may be amorphous and hence more easily dispersed than highly regular dense cytoplasmic inclusion bodies [34], [35]. The various forms of recombinant Con A have also been directed to the periplasm, as in Min et al. [5]. Therefore it could not be assumed that conventional isolation procedures [36] for cytoplasmic inclusions would be adequate. Furthermore, in developing jack bean seeds Con A accumulates in protein bodies [37] in an insoluble but active form (since a saline extract can bind to dextran columns) [4], [38]. Thus, the possibility that some of the recombinant lectin in the insoluble bacterial fraction is likewise correctly folded and active but has precipitated in the confines of the periplasm cannot be excluded. Any such active form may specifically bind cell components of appropriate structure, in addition to any non-specific binding which may also be shown by inactive forms of Con A. Thus there is a need to remove interfering bacterial substances from active as well as inactive Con A.

Incorrectly folded aggregated proteins are expected to remain insoluble in the absence of very harsh conditions so that e.g. chaotropic denaturants or very strong alkali are avoided here. Native Con A is soluble in acidic conditions, but is inactivated and aggregates at pH>8.5 [38], [39]. Low ionic strength (I<0.3) decreases the stability and solubility of native Con A [40], and divalent cations ($Mn^{2+}$ and $Ca^{2+}$) are required to maintain its activity [38]. Therefore, a buffer about pH 9, effective at low ionic strength and compatible with a metal-chelating agent, is required.

Figure 13:
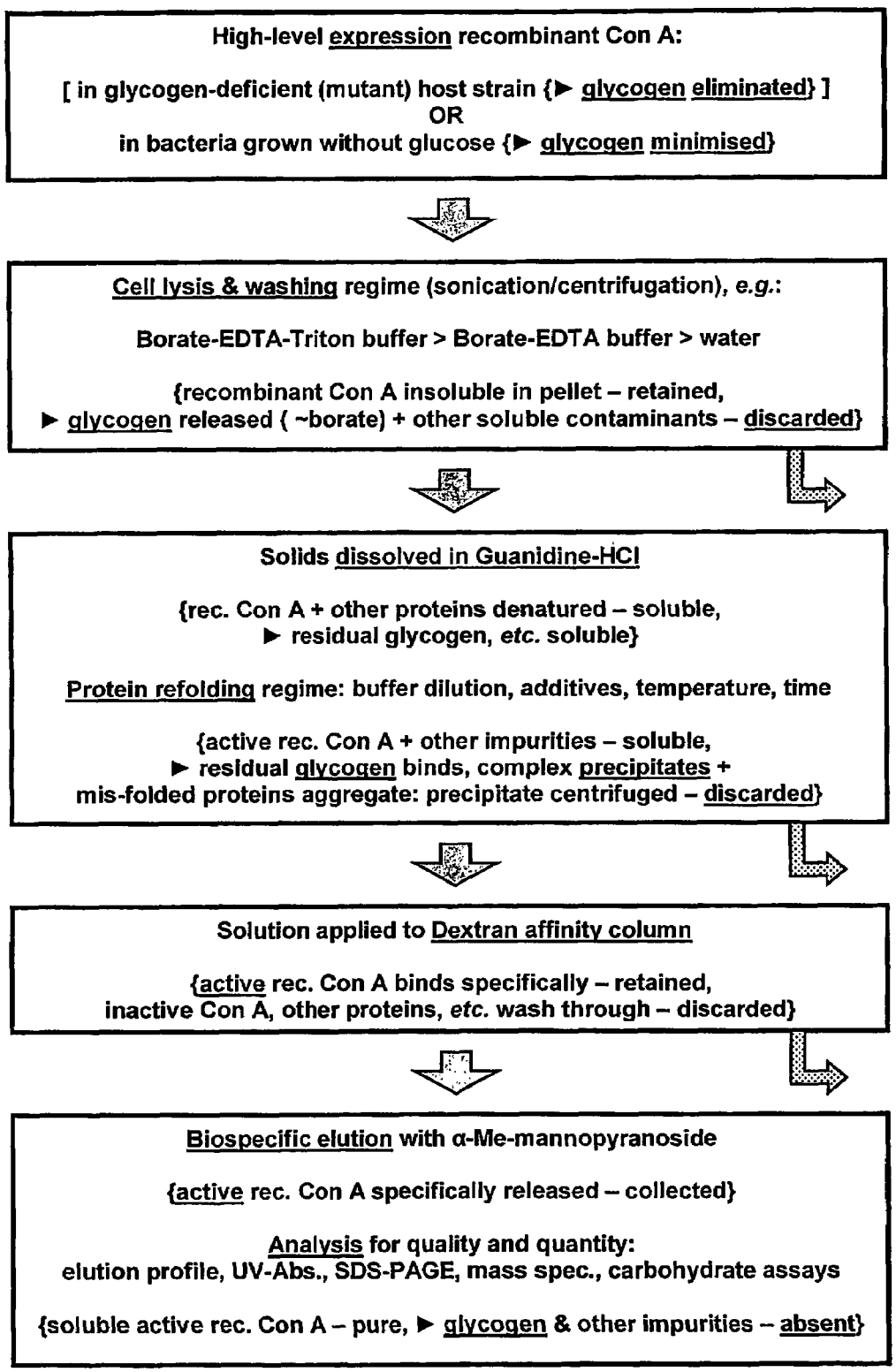
FIG. 13 depicts scheme of preferred embodiments of method for example of recombinant forms of Concanavalin A.

Thus, in the first aspect the present invention provides a method of obtaining a recombinant glucose binding protein expressed in non-plant host cells comprising reducing the glycogen content of a lysate of said cells. As used herein "reducing" means eliminating or minimising the amount of glycogen present. The level of glycogen must be reduced to such an extent that a glucose binding protein can be isolated. The glycogen can be eliminated by preventing the biosynthesis of glycogen during the growth of the host cells, for example by using host cells which are incapable of producing glycogen due to mutations in genes for its synthesis [31]. Similarly, cells can be grown in conditions such that the production of glycogen is minimised, i.e. growing the cells in the absence of glucose or any other assimilable carbohydrate or carbon-source that may be accumulated as glycogen. Alternatively the glycogen and the recombinant glucose-binding protein can then be separated from one another, for example by washing the cell lysate in appropriate solutions, and thus removing the glycogen. A further opportunity for removal of residual glycogen is afforded after refolding the recombinant protein, by ensuring appropriate conditions for the precipitation and removal by centrifugation of any glycogen in complex with active glucose-binding protein. FIG. 13 shows the various ways in which the glycogen content of a lysate of non-plant host cells can be reduced.

In one preferred embodiment the washing method comprises using a low ionic strength buffer with a pH between 8.5 and 9.5. In a preferred embodiment the pH of the buffer is 9.05 to 9.25 and I<0.1.

The term "low ionic strength" as used herein means I<0.3, and preferably I<0.1 [38], [40].

Two buffering compounds have been found that meet the criteria above: CHES {2-(cyclohexylamino)-ethanesulphonic acid} with pK=9.50, or borate {as $Na_2B_4O_7.10H_2O$, disodium tetraborate decahydrate or borax with pK=9.24 (at 25° C., [41]). Experiments at pH 9.1 using CHES showed that this approach would work, but borate gave better indications of protein purity and was preferred over CHES. Borate is used at a pH close to its pK to maximize its buffering capacity at a low ionic strength [41]. The disodium salt of ethylene-di-amine-tetra-acetic acid ($EDTA.Na_2$) was included to chelate metal ions [41].

Thus in one preferred embodiment of the invention the buffer comprises CHES or borate.

The solution should dissolve carbohydrates including polysaccharides (glycogen) and small cell wall fragments, nucleic acids for example DNA, RNA and any fragments and derivatives, lipid materials such as lipopolysaccharides, membrane and other lipids. As the desired protein is insoluble, but the interfering materials, especially the carbohydrates are soluble, the protein can be easily separated from the contaminants.

Borate has useful properties with regard to the above. It readily forms negatively charged soluble complexes with neutral polysaccharides and has long been used for their separation [42]. Borate is also used (together with EDTA) as a component of buffers to dissolve DNA and RNA during their electrophoretic separation [43]. EDTA is also used to liberate lipopolysaccharide from *E. coli* [32]. The non-ionic detergent Triton X-100 was included in the first washing step to solubilise lipid materials [41].

In addition the solution should ideally provide conditions which promote the release of any specifically-bound contaminants by any active Con A present. The solution should compete with or release molecules recognised by Con A. This property should also be easily eliminated and not carried through to the affinity chromatography steps, so that it could not then prevent the desired binding to dextran beads and recovery of active refolded lectin.

Release of any specifically-recognised substances as above might be achieved by using a monosaccharide to compete for the binding site of Con A. However, another advantageous feature of borate is its ability to inhibit precipitation of polysaccharides by Con A [44] and to specifically release carbohydrates (including glycogen) tightly bound to Con A [45], [46], and bound to closely related lectins [47], [48]. Borate can also be easily removed from precipitates by aqueous washing.

In one particularly preferred embodiment the buffer comprises borate, more preferably 20 mM Borax (FIGS. 5-8).

The term "glucose binding protein" refers to any protein, polypeptide, or fragment thereof which specifically binds to glucose, i.e. has a binding affinity for glucose as might be indicated by a dissociation constant ($K_d$) of about $10^{-2}$ M and all values below this.

Such proteins may include any enzymes of glucose, glycogen or starch metabolism, receptors and lectins, in particular Con A. The present invention also encompasses various forms of these proteins, such as: pre-pro-proteins, pro-proteins, mature (fully processed) proteins, and any tetrameric, dimeric or monomeric forms howsoever modified in their quaternary structure. Mutant forms of the protein that are still active, i.e. retain the ability to bind to glucose are also covered by the invention. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another. Such mutants can include fragments of the protein, provided that the ability to bind glucose is retained.

Furthermore, such proteins may have one or more binding sites for specific sugars (including glucose) ie. they may be multivalent, where valency refers to the number of carbohydrate binding sites per protein molecule. Any modified or mutant recombinant forms where the valency has been altered or reduced below that naturally found, but where at least one active site has been retained, are covered by this invention. For instance in the case of Con A, the valency might be reduced below 4 active sites to 3, 2, or 1 active sites per protein molecule—whether or not the number of subunits was also varied. Provided one or more active sites is retained in the assembled quaternary structure regardless of the number of subunits (protomers, monomers) comprising that structure, then the present invention encompasses any such variable and low valency forms.

In another aspect the present invention provides a recombinant glucose binding protein substantially free of glycogen, and optionally other impurities. The protein is preferably a lectin, more preferably Concanavalin A a precursor form or a mutant or variable valency or low valency form thereof.

"Substantially free" as used herein means that there is less than 5% (w/w protein) non-dialysable carbohydrate (including glycogen) present, more preferably less than 2%, 1% or 0.5% (w/w protein) non-dialysable carbohydrate (including glycogen); or less than 5% (w/w protein) glycogen present, more preferably less than 2%, 1%, 0.5%, 0.2% or 0.1% (w/w protein) glycogen. Most preferably the protein is contaminated with less than 1% (w/w) impurities including glycogen.

In a further aspect the present invention provides the use of a recombinant glucose binding protein obtained by a method of the present invention in a system where the presence of glycogen would interfere with the binding of said glucose binding protein to another ligand. Such systems may find use for example in forming Con A-multivalent ligand matrices. The proteins of the present invention can also be used to measure the concentration of glucose in a sample. Thus the use is preferably a method for measuring glucose concentration. In one preferred embodiment the recombinant glucose binding protein is expressed from a coding sequence derived from a leguminous plant, preferably of the genus *Canavalia*, more preferably *Caiavalia ensiformis*. The coding sequence can be replicated or derived from a DNA or RNA molecule isolated from the plant material, or it can be completely chemically synthesised, using well known methods. The coding sequence can comprise DNA or RNA. The recombinant protein is preferably a glucose binding lectin, preferably a Con A-like lectin, more preferably Con A or a precursor form or a mutant or variable valency or low valency form thereof. Preferably the Con A is substantially free of Con A sequence-related polypeptides or fragments. "Substantially free" means more than 95%, preferably more than 97.5%, more preferably more than 99% of the protein present comprises intact Con A. More preferably the Con A is the mature tetrameric tetravalent form of the protein. The protein is also preferably substantially free of glycogen.

The protein preferably forms part of a glucose biosensor such as those described in the prior art [7-19] The generation of the signal proportional to the concentration of glucose present may be effected by any method such as viscometric methods, and fluorescence-based methods including FRET. These methods all rely on competitive binding between the glucose present in the sample and an analyte-analogue. Analyte-analogues may consist of a glucose derivative, e.g. α-methyl glucopyranoside, a glucose polymer or polysaccharide containing glucose, for example dextran. Alternatively the analyte-analogues can comprise a carrier molecule covalently linked to glucose or a glucose derivative. The carrier molecule is preferably a protein, for example a serum albumin.

The present invention will now be described in the following Example, which refer to the figures listed below.

FIG. 1. Dextran affinity chromatography elution profile for recombinant mature Con A refolded from the bacterial cell fraction insoluble in MOPS-metals buffer.

The vertical axis represents Absorbance at 280 nm ($A_{280}$) with full scale (100%) set to 0.2 $A_{280}$. The horizontal axis represents elution volume with time progressing from left to right (flow rate=0.2 ml/min, chart speed=0.5 mm/min).

Refolded protein (obtained from 100 ml bacterial culture) in MOPS-metals buffer (45 ml) was pumped slowly (0.1 ml/min) down a column of Sephadex G-75 as in Min et al. [5]. The column was washed to baseline $A_{280}$ at 0.5 ml/min and then eluted as shown: firstly with 10 mM, and then with 100 mM methyl α-D-mannopyranoside at 0.2 ml/min.

A typical $A_{280}$ profile is shown with a small broad peak eluting at the lower monosaccharide concentration and further material eluting progressively after the competing monosaccharide concentration is raised. (The soluble fraction from these cells applied directly to the affinity column produced material which could only be eluted at 100 mM methyl α-D-mannopyranoside.) Peak sizes and shapes were very variable in different experiments.

FIG. 2. UV spectral wavelength scan after affinity chromatography of recombinant mature Con A (refolded from the bacterial cell fraction insoluble in MOPS-metals buffer).

Peak fractions (F4, F5) eluted by 10 mM methyl α-D-mannopyranoside from a dextran affinity column were examined by UV spectroscopy in a Beckman DU-650 spectrophotometer using the elution buffer as a reference. A commercial sample (Sigma Type IV) of native Con A purified from jack beans was included as a standard (ST) for comparison, showing a typical protein absorption spectrum with maximal absorbance around 280 nm. Peak fractions (F4, F5) show a relatively flat spectrum with no such maximum. The ratio ($A_{280}/A_{260}$) for each scan was F4, 0.92; F5, 0.96 and ST, 1.72. This indicates entrapment of nucleic acid-derived materials in these peak fractions which had been eluted from the dextran column by a monosaccharide highly specific for the binding site of Con A.

Figure 3:
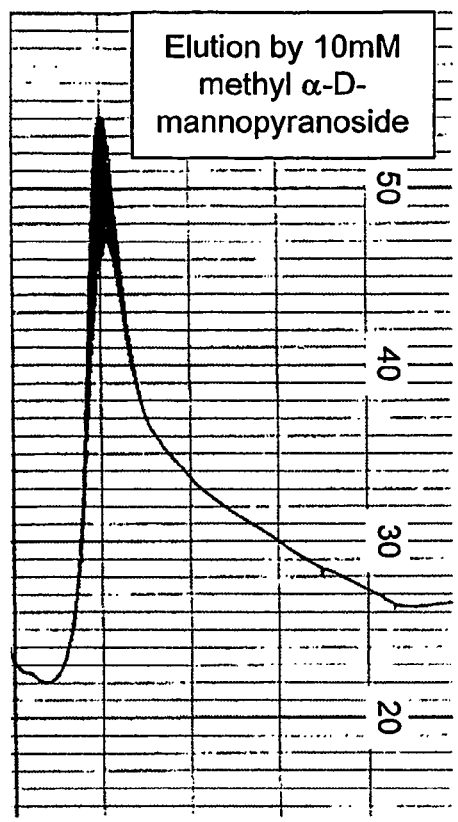
FIG. 3 depicts dextran affinity chromatography elution profile for recombinant mature Con A refolded from the fraction insoluble in MOPS-metals buffer obtained from glycogen-deficient mutant bacterial cells.

FIG. 3. Dextran affinity chromatography elution profile for recombinant mature Con A refolded from the fraction insoluble in MOPS-metals buffer obtained from glycogen-deficient mutant bacterial cells.

The vertical axis represents Absorbance at 280 nm ($A_{280}$) with full scale (100%) set to 0.5 $A_{280}$. The horizontal axis represents elution volume with time progressing from left to right (flow rate=0.2 ml/min, chart speed=0.5 mm/min).

Refolded protein (obtained from 250 ml bacterial culture) in MOPS-metals buffer (90 ml) was pumped slowly (0.1 ml/min) down a column of Sephadex G-75 as in Min et al. [5]. The column was washed to baseline $A_{280}$ at 0.5 ml/min and then eluted with 10 mM methyl α-D-mannopyranoside at 0.2 ml/min.

A typical $A_{280}$ elution profile is shown with a broadened noisy peak. (The soluble fraction applied directly to the affinity column produced small peaks eluting at 10 mM methyl α-D-mannopyranoside if glycogen-deficient mutant cells were grown at reduced temperature (28° C. instead of 37° C.).) Peak sizes and shapes were variable in different experiments.

Figure 4:
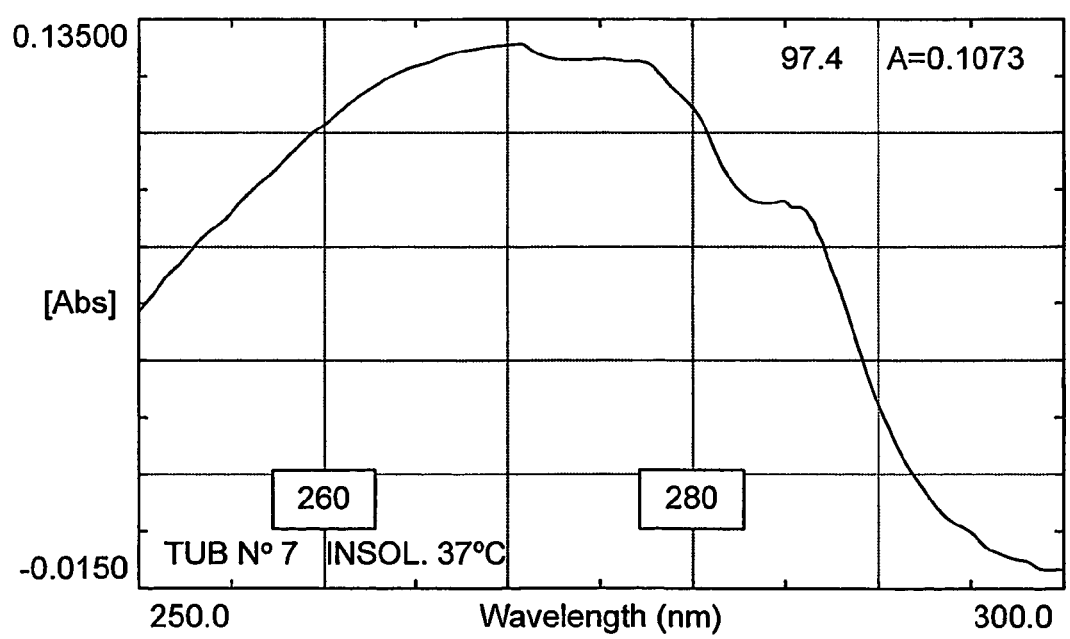
FIG. 4 depicts UV spectral wavelength scan after affinity chromatography of recombinant mature Con A (refolded from the fraction insoluble in MOPS-metals buffer obtained from glycogen-deficient mutant bacterial cells)

FIG. 4. UV spectral wavelength scan after affinity chromatography of recombinant mature Con A (refolded from the fraction insoluble in MOPS-metals buffer) obtained from glycogen-deficient mutant bacterial cells.

A peak fraction eluted by 10 mM methyl α-D-mannopyranoside from dextran affinity chromatography was examined by UV spectroscopy in a Beckman DU-650 spectrophotometer using the elution buffer as a reference. This scan is now closer to pure Con A than the peak fractions shown in FIG. 2, but still shows elevated absorbances at wavelengths below 280 nm compared to pure Con A. The ratio ($A_{280}/A_{260}$) obtained was 1.06, well below the value for pure Con A (FIG. 2). Elimination of glycogen synthesis from the host cells expressing recombinant Con A appears to have improved the product, but not solved all the problems of contaminating materials.

Figure 5:
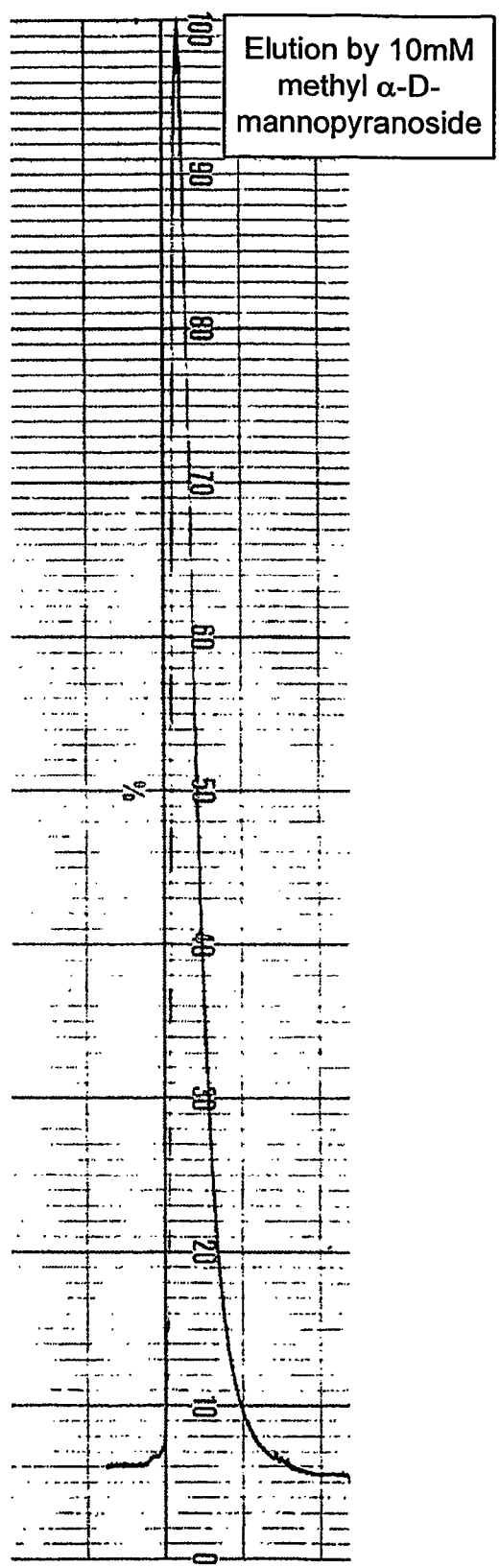
FIG. 5 depicts dextran affinity chromatography elution profile for recombinant mature Con A refolded after using the Borate Wash Method.

FIG. 5. Dextran affinity chromatography elution profile for recombinant mature Con A refolded after using the Borate Wash Method.

The vertical axis represents Absorbance at 280 nm ($A_{280}$) with full scale (100%) set to 0.2 $A_{280}$. The horizontal axis represents elution volume with time progressing from left to right (flow rate=0.2 ml/min, chart speed=0.5 mm/min).

Insoluble material, obtained from 100 ml bacterial culture (not a glycogen-deficient mutant) after processing by the Borate Wash Method, was refolded in MOPS-refolding buffer (45 ml) and then pumped slowly (0.1 ml/min) down a column of Sephadex G-75. The column was washed to baseline $A_{280}$ at 0.5 ml/min and then eluted with 10 mM methyl α-D-mannopyranoside at 0.2 ml/min.

A typical $A_{280}$ profile is shown and the sharp symmetrical peak indicates that a single homogeneous component has been specifically eluted by the competing monosaccharide. No further $A_{280}$-detectable material was eluted if the concentration of methyl α-D-mannopyranoside was raised to 100 mM. Sharp symmetrical peaks were consistently obtained in repeated experiments, with the shape invariant and the size (area) dependent on the amount of recombinant Con A derivative being purified.

Figure 6:
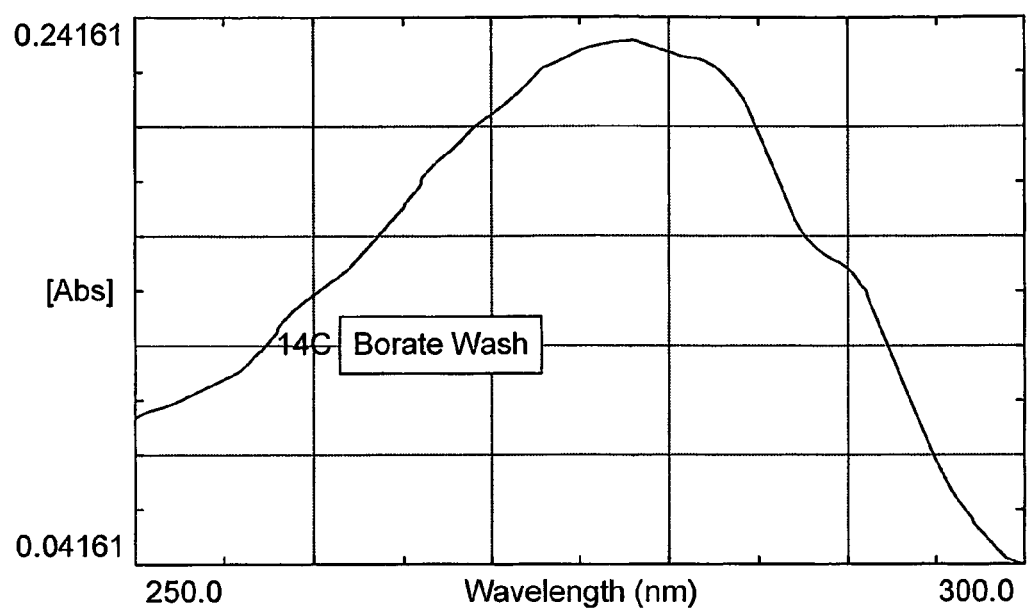
FIG. 6 depicts UV spectral wavelength scan following affinity chromatography of recombinant mature Con A refolded after using the Borate Wash Method.

FIG. 6. UV spectral wavelength scan following affinity chromatography of recombinant mature Con A refolded after using the Borate Wash Method.

A typical peak fraction eluted by 10 mM methyl α-D-mannopyranoside from dextran affinity chromatography examined by UV spectroscopy in a Beckman DU-650 spectrophotometer using the elution buffer as a reference. The shape of the absorption spectrum, and the ratio ($A_{280}/A_{260}$) of 1.68, now compare very well with pure plant-derived Con A (FIG. 2). UV spectra with these characteristics were consistently obtained in repeated experiments employing the Borate Wash Method and indicate that it removes substances previously found to interfere with purification of recombinant Con A variants.

Figure 7:
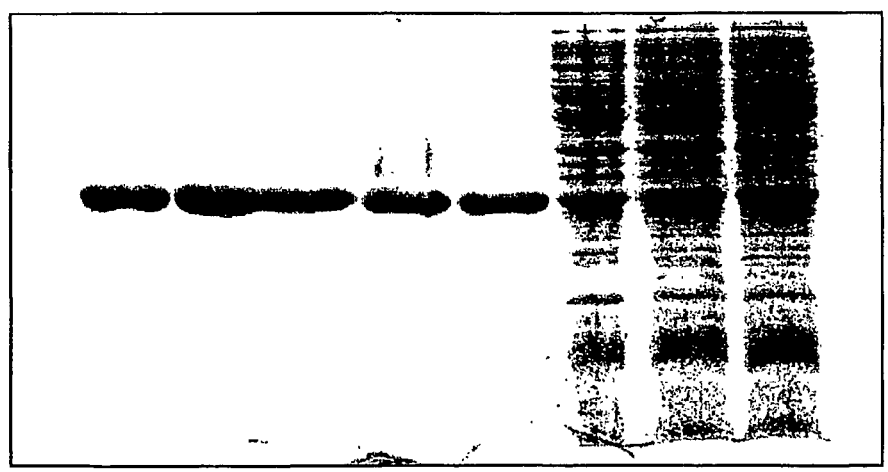
FIG. 7 depicts stained SDS-PAGE showing repeated purification experiments on recombinant mature Con A using the Borate Wash Method.

FIG. 7. Stained SDS-PAGE showing repeated purification experiments on recombinant mature Con A using the Borate Wash Method.

Sodium Dodecyl Sulphate—Poly Acrylamide Gel Electrophoresis (SDS-PAGE) was used to separate proteins according to subunit molecular weight [49] on a 15% gel which was then stained with Coomassie Blue to show all proteins present. The first five lanes (starting from the left-hand side) each show individual purification experiments using the Borate Wash Method followed by dextran affinity chromatography. Only one band is seen in every case indicating that protein homogeneity has been achieved. The gel has been deliberately overloaded to demonstrate the absence of minor protein bands due to contamination or degradation of the recombinant Con A. The last three lanes show total proteins (extracted by boiling in SDS-sample buffer) from bacterial cells expressing recombinant mature Con A. The degree of protein purification and consistency of the results is clearly evident.

Figure 8:
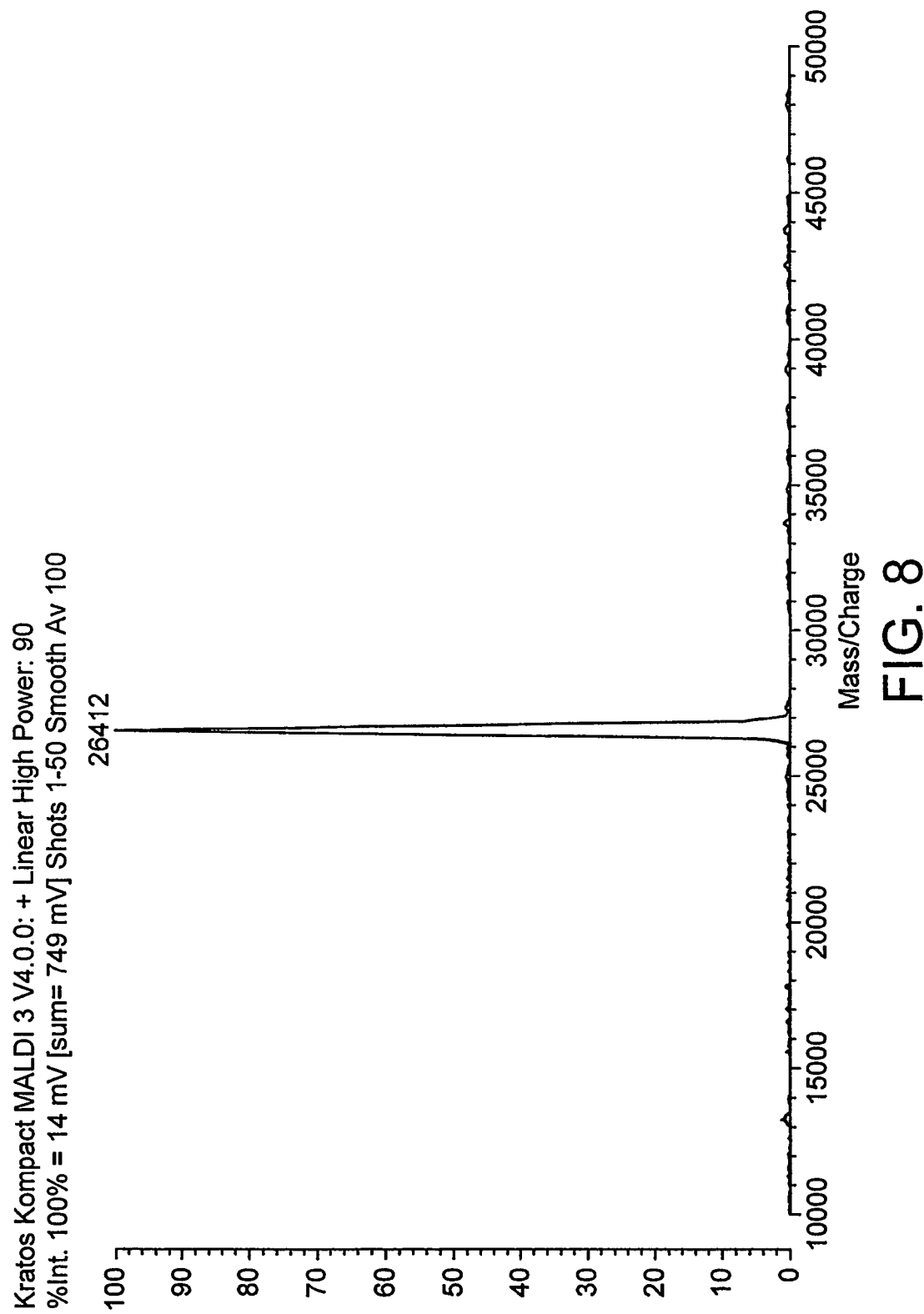
FIG. 8 depicts MALDI-TOFF mass spectrogram following affinity chromatography of recombinant mature Con A refolded after using the Borate Wash Method.

FIG. 8. MALDI-TOF mass spectrogram following affinity chromatography of recombinant mature Con A refolded after using the Borate Wash Method.

Matrix Assisted Laser Desorption Ionisation—Time of Plight (MALDI-TOF) mass spectrometry was used to analyse a typical peak fraction eluted by 10 mM methyl α-D-mannopyranoside from dextran affinity chromatography after using the Borate Wash Method. A Kratos Kompact MALDI 3 instrument was used in linear, positive ion mode. The sample as eluted (protein concentration=0.12 mg/ml) was applied directly to the grid with no further treatment. Sinapinic acid was used as the matrix and data were acquired from 50 shots with a $N_2$-laser. Bovine Serum Albumin was used as a calibration protein (not shown).

A single species is seen with the expected mass for this version of recombinant mature Con A. It is clearly evident that there are no other molecules detected across the Mass/Charge range of 10,000-50,000 analysed here.

Figure 9:
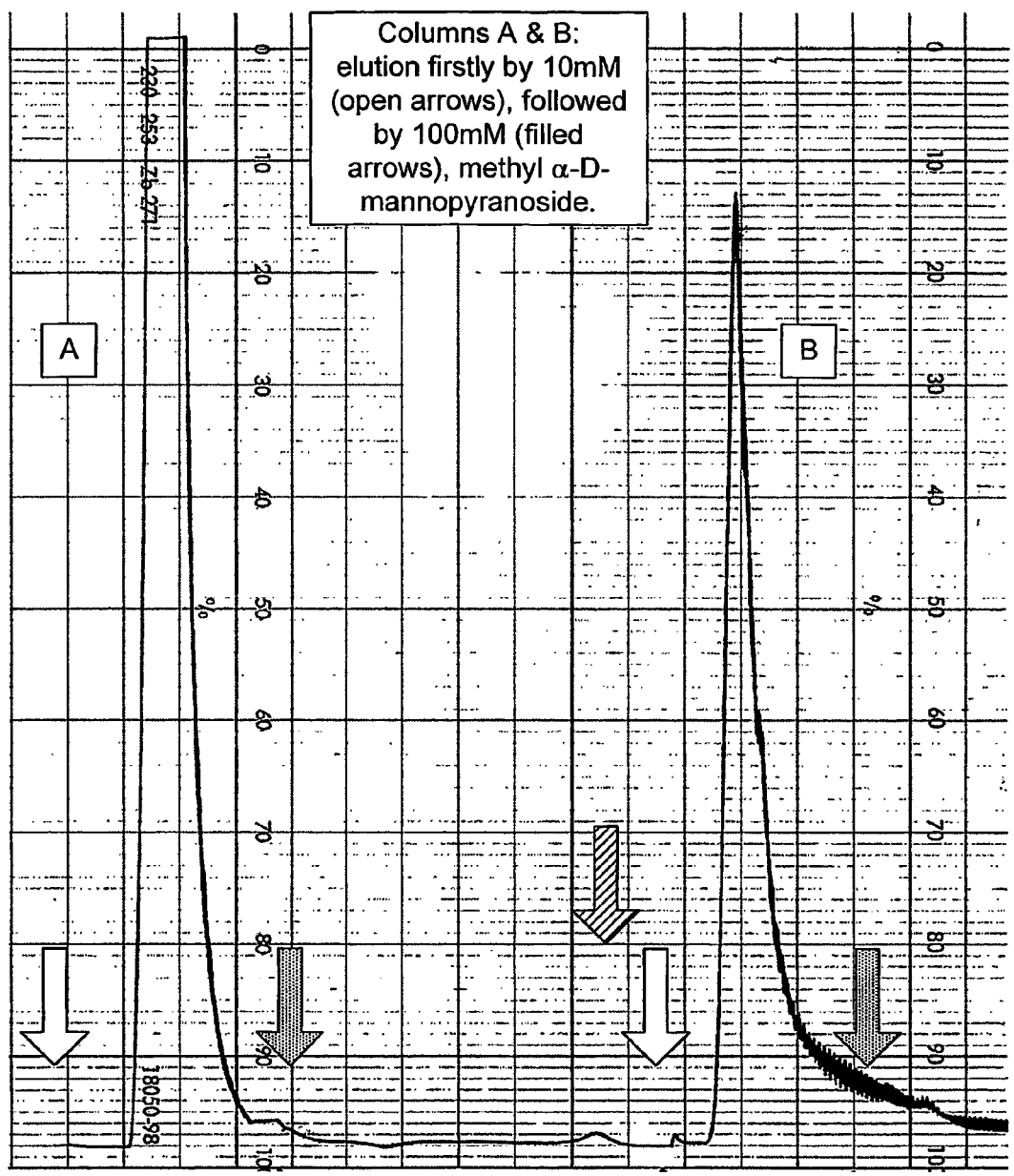
FIG. 9 depicts dextran affinity chromatography elution profiles for recombinant mature Con A: performance of the Borate Wash Method on (A) cells grown in medium without added glucose and (B) glycogen-replete cells.

FIG. 9. Dextran affinity chromatography elution profiles for recombinant mature Con A: performance of the Borate Wash Method on (A) cells grown in medium without added glucose and (B) glycogen-replete cells.

The vertical axis represents Absorbance at 280 nm ($A_{280}$) with full scale (100%) set to 2.0 $A_{280}$. The horizontal axis represents elution volume with time progressing from left to right (flow rate=0.2 ml/min, chart speed=0.5 mm/min).

Insoluble material, obtained from 500 ml bacterial cultures (not a glycogen-deficient mutant) after processing by the Borate Wash Method, was refolded in MOPS-refolding buffer (180 ml) and then pumped slowly (0.1 ml/min) down a column of Sephadex G-75. The column was washed to baseline $A_{280}$ at 0.5 ml/min and then eluted successively with 10 mM, then 100 mM methyl α-D-mannopyranoside at 0.2 ml/min.

The $A_{280}$ profile for column A (culture without glucose) shows a sharp symmetrical peak which has exceeded the measuring scale of the monitor due to the high yield obtained (21.9 mg protein per liter culture). Column B (culture with 1% glucose) shows a much reduced irregular peak with a noisy tail as material continues to elute when the concentration of methyl α-D-mannopyranoside is raised to 100 mM. Estimated yield from column B was 6.7 mg protein per liter culture.

Figure 10:
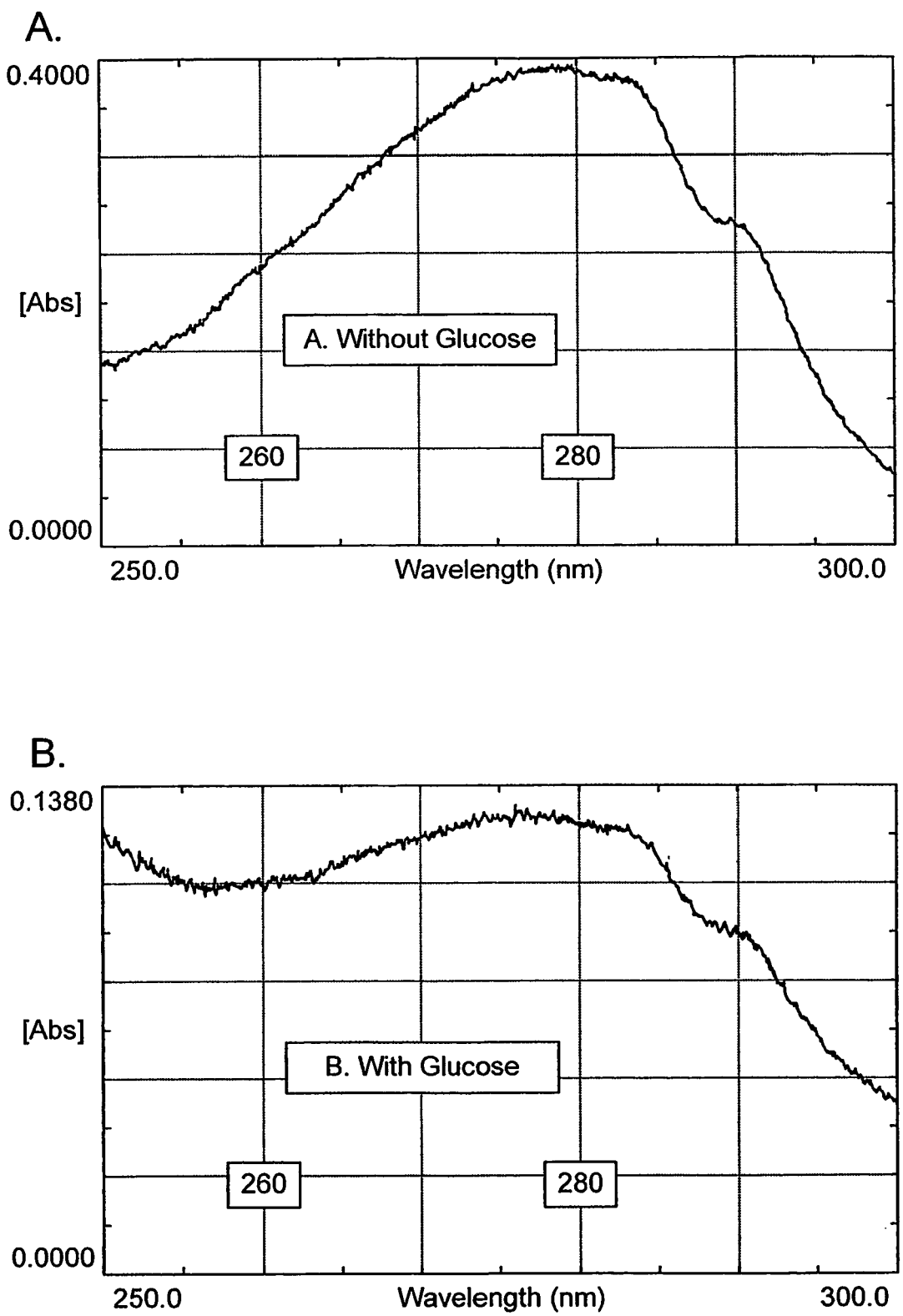
FIG. 10 depicts UV spectral wavelength scans following affinity chromatography of recombinant mature Con A: performance of the Borate Wash Method on (A) cells grown in medium without added glucose and (B) glycogen-replete cells.

FIG. 10. UV spectral wavelength scans following affinity chromatography of recombinant mature Con A: performance of the Borate Wash Method on (A) cells grown in medium without added glucose and (B) glycogen-replete cells.

The peaks eluted by 10 mM methyl α-D-mannopyranoside in FIG. 9 were examined by UV spectroscopy in a Beckman DU-650 spectrophotometer (after 5-fold dilution in elution buffer and using elution buffer as a reference). The scan for A (from culture without glucose) is shown on an absorbance scale of 0-0.400 whereas that for B (from culture with 1% glucose) is on an absorbance scale of 0-0.138. The shape of absorption spectrum A with the ratio ($A_{280}/A_{260}$) of 1.71 {corresponding to ≦0.1% nucleic acid (w/w protein) [41]} is consistent with numerous applications of the Borate Wash Method (FIG. 6). However, scan B shows a flattened shape with the ratio ($A_{280}/A_{260}$)=1.15 {corresponding to 2.05% nucleic acid (w/w protein) [41]} similar to results Rig. 2) from the prior method [5] used on cultures grown without glucose.

Figure 11:
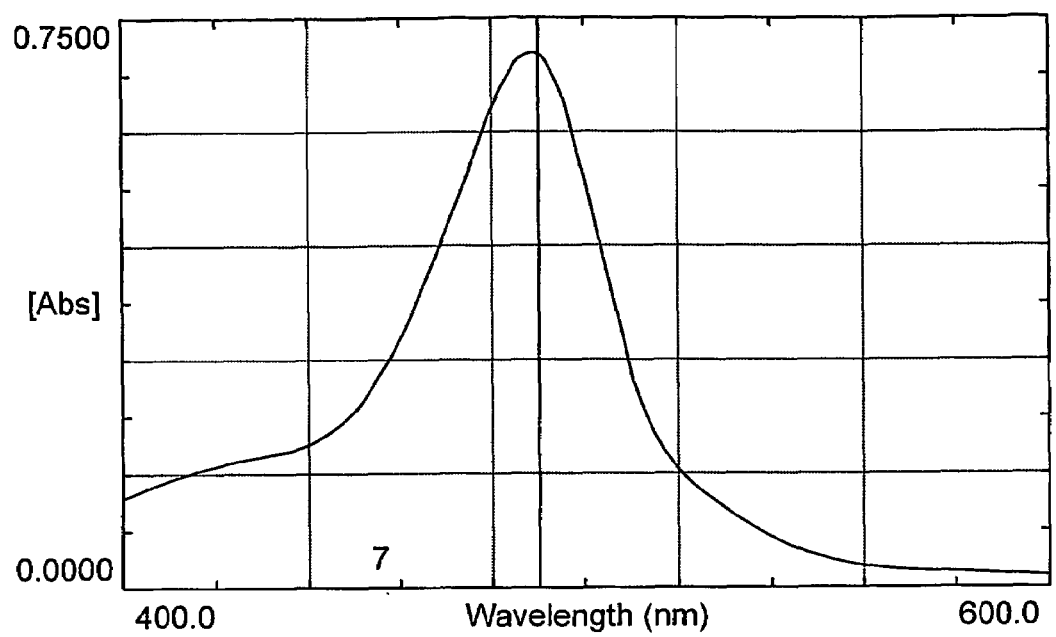
FIG. 11 depicts phenol-sulphuric acid analysis for non-dialysable carbohydrate present in a recombinant mature Con A preparation from glycogen-replete cells made using the Borate Wash Method.

FIG. 11. Phenol-sulphuric acid analysis for non-dialysable carbohydrate present in a recombinant mature Con A preparation from glycogen-replete cells made using the Borate Wash Method.

The preparation from glucose-grown cells (FIGS. 9B and 10B) was dialysed extensively against 1 M NaCl (6 changes over 6 days), whereupon a flocculent precipitate formed in the previously clear solution. This was resuspended and carbohydrate was determined by the Phenol-Sulphuric Acid Method [50], [51]. An absorption spectrum (400-600 nm, cursor line at 490 nm) is shown for a sample two-fold diluted with 1 M NaCl before reaction. This shows the characteristic shape for the orange-coloured products formed by reaction of carbohydrates in phenol-sulphuric acid {e.g. curve for starch in FIG. 5 of ref. [50]}. The non-dialysable total carbohydrate content of this sample was 25.7% (w/w protein). Its glycogen content was also specifically and independently determined as 27.5% (w/w protein) using an enzymatic coupled assay system [52], [53] (see Results).

Figure 12:
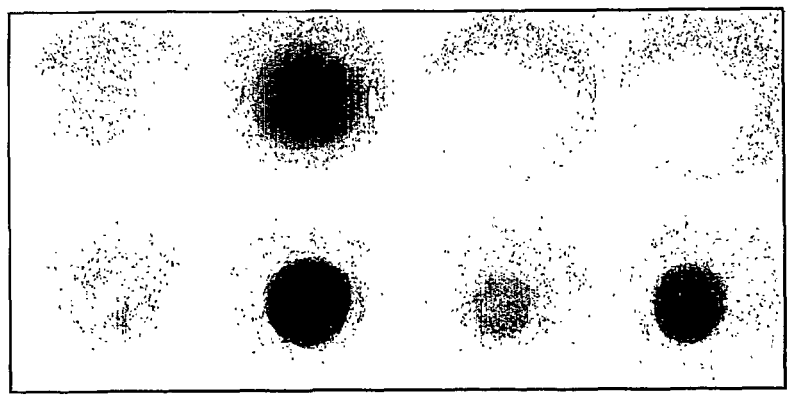
FIG. 12 depicts demonstration by iodine color reaction of the presence of glycogen in precipitated material formed during the refolding of recombinant mature Con A after performing the Borate Wash Method on cultures grown with or without added glucose.

FIG. 12. Demonstration by iodine colour reaction of the presence of glycogen in precipitated material formed during the refolding of recombinant mature Con A after performing the Borate Wash Method on cultures grown with or without added glucose.

Material precipitating during the refolding step is removed by centrifugation (and normally discarded) before applying the clear supernatant to dextran affinity columns. Refolding precipitates (from processing 500 ml bacterial cultures—not a glycogen-deficient mutant) were collected and resuspended in 5 ml MOPS-metals buffer before removing samples (4 drops) of the slurry formed on settling to a spotting tile. These were covered with 4 drops of $I_2$/KI solution (2 g KI+1 g $I_2$ in 300 ml water), mixed gently and photographed within a few minutes before colours faded.

Top row, left to right: MOPS-metals buffer only (negative control), Pure glycogen (Sigma Type II) 0.5% (w/v) in this buffer (positive control).

Bottom row, left to right, refolding precipitates from 4 cultures grown: without glucose, with glucose, without glucose, with glucose, respectively. The latter two samples correspond to preparations A and B in FIGS. 9 and 10.

Presence of glycogen is shown by the characteristic red-brown colouration, with a weaker reaction from cultures grown without glucose. Cultures grown with glucose produced refolding precipitates showing a much stronger but variable reaction: less glycogen was present in the rightmost precipitate which correlated with a poorer quality Con A preparation than that from the other glucose-grown culture which showed a stronger reaction in the precipitate.

FIG. 13. Scheme of preferred embodiments of method for example of recombinant forms of Concanavalin A.

Abbreviations and terms used: UW-Abs., Ultra-Violet Absorption Spectroscopy; SDS-PAGE, Sodium Dodecyl Sulphate—Poly Acrylamide Gel Electrophoresis; mass spec., mass spectrometry; carbohydrate analysis, phenol-sulphuric acid method & enzymatic analysis for glycogen. Details and references are given in text.

EXAMPLE

Borate Wash Method for Purifying Recombinant Con A Variants from *E. coli*.

Borate Wash Buffer (1 liter).

20 mM borax (7.63 g $Na_2B_4O_7.10H_2O$, disodium tetraborate decahydrate)

5 mM EDTA (1.86 g $Na_2EDTA.2H_2O$, ethylene-diamine-tetra-acetic acid, disodium salt, dihydrate)

Made up to 1 liter with water, the pH was 9.1-9.2 and did not need to be adjusted.

MOPS-Metals Buffer (1 liter).

1 M NaCl (58.44 g sodium chloride)

50 mM MOPS (10.5 g 3-(N-morpholino)propanesulphonic acid)

Made up to 1 liter with water and pH adjusted to 7.0 at room temperature using 5 M NaOH. Calcium and manganese were added (1 ml each of 1 M $CaCl_2$ and 1 M $MnCl_2$) giving a final concentration for each metal of 1 mM. (To prevent their precipitation the $Ca^{2+}$ or $Mn^{2+}$ must not be added before the pH is adjusted.) Sodium azide (0.1 g $NaN_3$) was added as a preservative.

Refolding Buffer.

The same MOPS-metals buffer made up as above was used, except that the final concentrations of calcium and manganese ions were 10 mM. Optionally, guanidine hydrochloride was sometimes included at a concentration of 0.25 to 0.50 M.

Bacterial Cell Collection.

The cells containing expressed recombinant Con A were harvested by centrifugation. Liquid culture (e.g. 500 ml) was spun at 6,400×g for 15 min at 4° C. The supernatant was poured off and discarded. The pelleted cells were stored in a −80° C. freezer until needed.

Extraction of Cells.

N.B. During this procedure, the correct volume ratios were maintained: for the frozen cell pellet obtained from each 250 ml aliquot of bacterial culture, a wash volume of 20 ml was used in steps 1 to 8 (below), and then 3 ml of 8 M guanidine-HCl were used to solubilise the pelleted material at step 10 (below). This 3 ml aliquot of extract was then refolded by 30-fold dilution in refolding buffer (90 ml).

1. The frozen cell pellet from 500 ml of liquid culture was thawed in 40 ml borate wash buffer containing 1% (v/v) Triton X-100.
2. The cell pellet was re-suspended as much as possible using a glass rod and divided equally between two centrifuge tubes (e.g. clear Oakridge type, 50 ml size).
3. Cells were broken open and DNA was sheared by 3×1 min ultra-sonication with tubes embedded in hard-packed ice. A sonicator (e.g. MSE Soniprep 150) set at maximum power and amplitude was used with the probe ~5 mm from the bottom of the tube. The suspension was allowed to cool for ~1 min between sonication periods.
4. The cell lysate was incubated at room temperature for 10-60 min with gentle mixing on an oscillating platform.
5. The cell debris was centrifuged at 48,400×g for 20 min at 4° C.
6. The supernatant was poured off carefully and the washed pellet was kept. The tube was drained by standing upside down on a piece of tissue paper.

N.B. The pellet was made up of two parts—a lower harder more opaque part and an upper less dense translucent part. The upper part contained most of the Con A (about 85%) and, particularly after washing with water (step 8 below), could become very light and was easily resuspended. Great care had to be taken when pouring off the supernatant in case any of the pellet was lost. After the second (step 7) and third washes (step 8), the tube was not stood upside down on tissue as some of the pellet might have been lost.

7. Each pellet (now equivalent to material from 250 ml bacterial culture) was resuspended in 20 ml borate wash buffer without Triton X-100 using 1×1 min sonication. It was then mixed at room temperature for 10-30 min, then centrifuged at 48,400×g for 20 min at 4° C., and drained, but not allowed to stand upside down.
8. The pellet was resuspended in 20 ml water using 1×1 min sonication and immediately centrifuged at 48,400×g for 20 min at 4° C. The supernatant was carefully discarded without disturbing the pellet.

9. The drained washed pellet was stored in a −80° C. freezer until needed.

N.B. Each of the successive washing steps above {firstly, borate wash buffer +1% (v/v) Triton X-100; secondly, borate wash buffer alone; thirdly, water} may be performed more than once if required to ensure purity of the final product.

10. The frozen pellet was thawed and a thin glass rod was used to break it up as finely as possible to give a creamy consistency. Each pellet was quickly dissolved in denaturant (3 ml of 8 M guanidine-hydrochloride made up in refolding buffer), as follows. The guanidine-hydrochloride solution was added carefully as a layer on top of the creamed pellet and then a plastic pasteur pipette was used to mix the layers rapidly by vigorously sucking up and expelling the liquid.

11. The guanidine-hydrochloride extract was mixed at room temperature for up to 1 h to ensure complete dissolution of material from the pellet. Sonication (1×1 min at room temperature) was sometimes carried out if undissolved material remained visible. At this stage, the two dissolved pellets were combined giving 6 ml extract (containing material processed from 500 ml bacterial culture).

12. The guanidine extract could be used immediately or frozen at −80° C. for storage.

Refolding.

1. The (thawed) guanidine extract was then refolded by rapidly diluting 30-fold into ice-cold refolding buffer: the 6 ml of guanidine extract was poured into 180 ml of refolding buffer while swirling to mix.
2. The refolding mixture was kept on ice for 1 to 2 h (optionally for longer).
3. The flask was then allowed to stand at room temperature for 1 to 2 h (optionally for longer) to complete the formation of any precipitate.
4. The refolded extract was centrifuged at 30,100×g for 20 min at 4° C., and the clear supernatant was then loaded onto a dextran affinity column, usually overnight. Optionally, Triton X-100 was sometimes added to the supernatant at a concentration of 0.5% (v/v) before column loading.

Dextran Affinity Chromatography.

1. A glass column (e.g. Pharmacia type C10, for a 10×65 mm bed) was packed with ~5 ml settled bed of Sephadex G-75 (Pharmacia, dry particle size 40-120 μm) equilibrated in MOPS-metals buffer (0.5 ml/min). A new bed of affinity matrix was packed for every purification.
2. Refolded extract (e.g. 180 ml) was pumped down the column overnight at 0.1-0.2 ml/min.
3. The column was washed (0.4-0.5 ml/min) with at least 10-bed volumes MOPS-metals buffer (>50 ml) with $A_{280}$ monitoring showing a flat baseline throughout.
4. The recombinant Con A variant was then eluted (0.2 ml/min) by 10 mM methyl α-D-mannopyranoside in MOPS-metals buffer. Fractions (10-15×1 ml) were collected while continuously monitoring $A_{280}$ (e.g. FIG. 5, 9A), and peak fractions were pooled.
5. Purified protein was quantified by UV-spectrophotometry ($A_{280}$). An absorption spectrum scan (250-300 nm) (e.g. FIG. 6, 10A) and other quality checks (e.g. FIGS. 7, 8 and see Results below) were performed.

Results

The practical difficulties of crude sample handling, problems of poor quality product, inconsistent yields and generally variable results with the purification method in the prior art [5] have been outlined earlier. An instance is illustrated in FIG. 1, where inhomogeneous material continues to elute from the dextran column when the competing monosaccharide concentration is raised. This is interpreted as being due to the formation of a high molecular weight complex [1] where Con A cross-links glycogen and may entrap other materials extracted from the bacterial cell. The multiple attachment sites for the dextran affinity matrix which would be available in such a complex by virtue of its Con A component would result in gradual detachment and disintegration of the complex in the presence of a sufficient concentration of competing monosaccharide. Although material can also be specifically released from dextran binding at lower eluant concentrations (FIG. 1), this clearly does not consist of protein alone (FIG. 2) and contains substances absorbing at 260 nm. This indicates that nucleic acids are associated and also suggests that these complexes vary in their avidity for the dextran matrix.

The variable and generally disappointing results (FIGS. 3 and 4) from glycogen-deficient expression hosts [31] were discussed earlier. Some improvement was seen compared to glycogen-containing cells, suggesting the likely role of glycogen in complexing with Con A but indicating that other contaminating materials were still associating with the protein when the prior art [5] was employed.

In contrast, the new Borate Wash Method facilitates processing of crude material and dramatically results in elution profiles (FIG. 5) and UV spectra (FIG. 6) corresponding to those of highly purified plant-derived Con A. This method consistently produces high quality protein (FIG. 7), which in the case of the recombinant mature form shown, does not contain any of the fragmented polypeptides present in the natural product (compare FIG. 2 of ref. [5]). The stained SDS-PAGE (FIG. 7) indicates purity with respect to protein components, whereas the mass spectrogram (FIG. 8) confirms that other molecules are absent. There do not appear to be precedents for the requirement (as indicated in the present work) to wash away carbohydrate components when preparing other proteins [34], [54] expressed in *Escherichia coli*.

As a further check on purity, samples of recombinant mature Con A prepared by the Borate Wash Method were analysed for carbohydrate content by two different techniques. Samples were first extensively dialysed against 1 M NaCl (6 changes over 6 days) to remove the affinity chromatography buffer containing the eluting monosaccharide (methyl α-D-mannopyranoside). The non-dialysable total carbohydrate was then determined by formation of furfurals using the Phenol-Sulphuric Acid Method [50], [51] calibrated with glucose standards made up in 1 M NaCl. Specific enzymatic glycogen determination was also performed using amyloglucosidase hydrolysis with the resultant glucose quantified by a hexokinase/glucose-6-phosphate dehydrogenase (NADPH) coupled assay [52], [53]. (Solutions were clarified by microcentrifugation before the spectrophotometric stage of this enzymatic assay.)

Eight preparations of recombinant mature Con A were expressed, processed by the Borate Wash Method and dialysed as described: values below are given as Mean±Standard Error of the Mean. The total non-dialysable carbohydrate was 0.33±0.03 (% w/w protein): this is near the detection limit of the Phenol-Sulphuric Acid Method [50]. Glycogen content was determined as 0.03±0.01 (% w/w protein), which value falls below the estimated detection threshold of the enzymatic coupled assay system [52]. The mean value of the ratio ($A_{280}/A_{260}$) for these dialysed samples was 1.75±0.02 and the nucleic acid content from spectroscopy (Warburg and Christian Method, p. 541 of ref. [41]) was barely estimable at 0.03±0.02 (% w/w protein).

An hypothesis that glycogen interferes with purification leads to two predictions: (i) that elimination of glycogen should improve the process, whereas (ii) increased cellular glycogen content should cause a deterioration. Glycogen-deficient (mutant) bacteria produced a small improvement (FIG. 4) in the prior method [5] but other impurities still remained. {The Borate Wash Method used on these glycogen-deficient mutant cells produces a high quality result as it does with non-mutant expression hosts (FIGS. 5-8).} The second prediction (ii) is more easily tested than (i) simply by supplementing the growth medium with 1% (w/v) glucose. This greatly increases glycogen accumulation [29], [30] in normal bacterial cells, so that its effects on the Borate Wash Method may then be evaluated (FIGS. 9-11).

Results from glucose-supplemented cultures were variable, but in all cases inferior to those from cultures without added glucose. Yields of product were greatly decreased with elution profiles distorted (FIG. 9B) and the eluted material containing nucleic acids (FIG. 10B). Glucose-supplementation has brought about a deterioration in the quantity and quality of recombinant Con A produced by the Borate Wash Method. This is very similar to the problems (FIGS. 1 & 2) evident in the prior method [5] applied to non-supplemented cells. During dialysis to remove methyl α-D-mannopyranoside, turbidity and precipitation was observed in samples produced from glucose-grown cells whereas solutions of product purified from cultures grown without glucose remained clear throughout dialysis. Non-dialysable carbohydrate was detectable [50] in turbid samples and sometimes reached high levels (FIG. 11) which could all then be accounted for as glycogen by enzymatic analysis [52].

These observations are all consistent with the view that when in vitro refolding succeeds in forming biologically active recombinant Con A, any glycogen also present in the refolding mixture forms a high molecular weight complex. This could entrap other molecules (such as nucleic acids, etc.). Any glycogen-Con A-impurity complex that precipitates would be removed by centrifugation before loading supernatant onto the affinity column. However, the extent of precipitation may be incomplete and variable—depending on the amount of glycogen present (and on conditions such as temperature [38])—so that soluble complex may be carried through to bind the dextran matrix (see earlier). Here it collects (as does free Con A) and is then specifically eluted in concentrated form which remains soluble due to its dissociation by methyl α-D-mannopyranoside. Subsequent removal of this monosaccharide by dialysis results in precipitation of the concentrated complex.

Although the Borate Wash Method is highly successful and consistent when applied to cultures grown without added glucose (FIGS. 5-8, 9A, 10A), it is clearly overwhelmed by glucose-supplementation (FIGS. 9B, 10B, 11, 12). The level of glycogen is not then sufficiently reduced before guanidinium solubilisation: precipitation by Con A during refolding (FIG. 12)—although greatly reducing yield—is incomplete and does not prevent carry-over of glycogen-complex to the affinity chromatography step. It is then too late to prevent contamination of the product. {The variation in glycogen detected in refolding precipitates from glucose-grown cells (FIG. 12) indicates a relationship between quality of the final product and amount of glycogen detected in the discarded material.}

It follows that a preferred pre-requisite for the successful application of the Borate Wash Method is expression of the recombinant protein in culture media without glucose, nor any other assimilable carbohydrate or carbon-source that may be accumulated as glycogen at enhanced levels by the bacterial cells [29], [30]. Whereas there does not appear to be a particular advantage in using glycogen-deficient mutants [31] as expression hosts provided that the washing and refolding regime described is followed carefully, glycogen-deficient mutant cells provide an additional optional safeguard against problems. When these mutant hosts are used, the same washing regime is followed since it has been shown to remove other impurities. However, there may be some other disadvantages associated with the use of glycogen-deficient bacteria, including yields and other quantitative aspects, which will not be discussed further here. A scheme to summarise preferred embodiments of method is shown in FIG. 13.

Although the prime concern here has been to demonstrate the superiority of the new Borate Wash Method in producing a high quality product, it has also been a very important contributing factor in increasing the quantities of recombinant protein obtainable. For example, yields of highly purified recombinant mature Con A of 10-20 mg from 1 liter of bacterial culture have recently been routinely obtained. This represents an improvement of between one and two orders of magnitude on the yields initially obtained for recombinant forms of Con A [5].

With regard to the use of recombinant forms of Con A in glucose sensors (the operating principles of which were described earlier) the following considerations now apply.

Firstly, any form of recombinant Con A that is active (i.e. is capable of specifically recognising and binding glucose and its derivatives—so encompasses precursor proteins) may in principle be used in a glucose sensor as a bio-receptor in place of native Con A. {"Native" is taken to mean Con A extracted from the plant source, usually the seeds of Jackbean (*Canavalia* sp.), and consists of the mature form of the protein normally present as a tetravalent tetramer at neutral pH [38].} Native Con A generally contains variable quantities of fragmented Con A polypeptides (e.g. shown in FIG. 2 of ref. [5]) derived from incomplete natural biosynthetic processing in planta [21]. The variable proportions are a consequence of the natural source and dependent on the vagaries of growth and harvesting conditions to which the crop was subjected. These fragmented forms are nevertheless co-folded into active subunits [55], and a single tetramer of the mature protein may include both cleaved (2-chain) and intact subunits in its quaternary structure. However, the 2-chain protein is de-stabilised [55] relative to the intact mature form (by about 15 kJ/mol or more) which might be problematic in long-term stability of implanted biosensors. A clear advantage in biosensor applications of all recombinant forms is the absence of such contaminating fragments, as illustrated in FIG. 7 for recombinant mature Con A. (It is of course essential to minimise any proteolysis attributable to the heterologous expression and purification conditions.) The benefits of a fragment-free product are additional to those of a secure, unlimited and highly consistent supply of any recombinant form of this protein.

Secondly, there is the issue of contaminants—other than polypeptides—and their effects on a glucose sensor. In this respect, glycogen contamination is germane to the proper and consistent operation of such a sensor since glycogen is itself an excellent highly specific cognate ligand for Con A [1] and so introduces another competing equilibrium into the system. The affinity of Con A for glycogen is greater than for free glucose and, in addition, glycogen is a multivalent polysaccharide having a branched structure with many terminal non-reducing ends which are the Con A receptors [1]. So glycogen is no ordinary non-specific impurity in this application since it competes with the analyte-analogue for binding to the bio-receptor [7], [8]. Thus glycogen is an unwanted second analyte-analogue impeding the core principle by which all these sensors operate. Variations in the amount of glycogen present in different samples of recombinant Con A will give variable interference in sensors made from it. This difficulty will be further complicated by varying levels of degradation of the contaminating glycogen so that the sizes of this molecule, its intrinsic receptor valency and the density of its distribution within the measuring assembly will be different from one sensor replicate to another. Thus, the properties of glycogen that are responsible for problems in purification of recombinant forms of Con A lead also to fundamental problems when it contaminates any binding application relying on Con A-carbohydrate recognition. These are just different facets of the same molecular properties and interactions and apply quite clearly to use of any active forms of recombinant Con A, so that glycogen contamination will render them unfit for use in a glucose sensing system.

REFERENCES

1 Goldstein, I. J. and Poretz, R. D. (1986) in The Lectins: Properties, Functions and Applications in Biology and Medicine (Liener, I. E., Sharon, N. and Goldstein, I. J., eds.), pp. 33-247, Academic Press, Orlando, London
2 Sumner, J. B. and Howell, S. F. (1936) Journal of Bacteriology 32, 227-237
3 Agrawal, B. B. L. and Goldstein, I. J. (1967) Biochim Biophys Acta 147, 262-71
4 Agrawal, B. B. L. and Goldstein, I. J. (1972) in Methods in Enzymology, vol. 28 (Ginsberg, V., ed.), pp. 313-318, Academic Press, New York
5 Min, W., Dunn, A. J. and Jones, D. H. (1992) EMBO J 11, 1303-7
6 Jones, D. H. (1995) in Perspectives on protein engineering and complementary technologies 1995 (Geisow, M. J. and Epton, R., eds.), pp. 70-73, Mayflower Worldwide, Birmingham
7 Eggins, B. R. (1996) Biosensors: an Introduction, John Wiley, Chichester, New York
8 Eggins, B. R. (2002) Chemical sensors & biosensors, Wiley, Chichester
9 Ehwald, R. (1996) Offenlegungsschrift DE 195 01 159 A1
10 Beyer, U., Ehwald, K.-E., Ehwald, R. and Thomas, A. (1999) Patent DE 197 14 087
11 Beyer, U., Schafer, D., Thomas, A., Aulich, H., Haueter, U., Reihl, B. and Ehwald, R. (2001) Diabetologia 44, 416-23
12 Schultz, J. S., Mansouri, S. and Goldstein, I. J. (1982) Diabetes Care 5, 245-253
13 Schultz, J. S. (1987) in Biosensors: Fundamentals and Applications (Turner, A. P. F., Karube, I. and Wilson, G. S., eds.), pp. 638-654, Oxford University Press, Oxford, N.Y., Toronto
14 Pickup, J., McCartney, L., Rolinsid, O. and Birch, D. (1999) BMJ 319, 1289-
15 Chick, W. L., Wolf, D. E. and Cardullo, R. A. (1991) (PCT) Patent WO 91/09312
16 Chick, W. L., Wolf, D. E. and Cardullo, R. A. (1994) (PCT) Patent WO 94/00602
17 Wolf, D. E. (1998) (PCT) Patent WO 98/55869
18 Wolf, D. E. (2001) Patent U.S. Pat. No. 6,232,130 B1
19 Wolf, D. E. (2000) (PCT) Patent WO 00/16099
20 Min, W. and Jones, D. H. (1992) FEBS Lett 301, 315-8
21 Min, W. and Jones, D. H. (1994) Nat Struct Biol 1, 502-4
22 Stubbs, M. E., Carver, J. P. and Dunn, R. J. (1986) J Biol Chem 261, 6141-4
23 Prasthofer, T., Phillips, S. R., Suddath, P. L. and Engler, J. A. (1989) J Biol Chem 264, 6793-6
24 van Eijsden, R. R., Hoedemaeker, F. J., Diaz, C. L., Lugtenberg, B. J., de Pater, B. S. and Kijne, J. W. (1992) Plant Mol Biol 20, 1049-58
25 Hoedemaeker, F. J., van Eijsden, R. R., Diaz, C. L., de Pater, B. S. and Kijne, J. W. (1993) Plant Mol Biol 22, 1039-46
26 Stryer, L. (1995) Biochemistry, W. H. Freeman, New York
27 Goldstein, I. J. and So, L. L. (1965) Arch Biochem Biophys 111, 407-14
28 Neidhardt, F. C. (1987) in *Escherichia coli* and *Salmonella typhimurium*: cellular and molecular biology (Neidhardt, F. C., ed.), pp. 3-6, American Society for Microbiology, Washington, D.C.
29 Preiss, J. and Romeo, T. (1989) Adv Microb Physiol 30, 183-238
30 Dawes, E. A. (1992) in Prokaryotic structure and function: a new perspective (47th Symposium of the Society for General Microbiology) (Dow, C. S., Coles, J. A. and Mohan, S., eds.), pp. 81-122, Cambridge University Press, Cambridge
31 Hengge-Aronis, R. and Fischer, D. (1992) Mol Microbiol 6, 1877-86
32 Nikaido, H. and Vaara, M. (1987) in *Escherichia coli* and *Salmonella typhimurium*: cellular and molecular biology (Neidhardt, F. C., ed.), pp. 7-22, American Society for Microbiology, Washington, D.C.
33 Mitraki, A. and King, J. (1989) Biotechnology (N Y) 7, 690-697
34 Georgiou, G. and Valax, P. (1999) Methods in Enzymology 309, 48-58
35 Bowden, G. A., Paredes, A. M. and Georgiou, G. (1991) Biotechnology (N Y) 9, 725-30
36 Marston, F. A. O. (1986) Biochem J 240, 1-12
37 Bowles, D. J. and Pappin, D. J. (1988) Trends Biochem Sci 13, 60-4
38 Liener, I. E. (1976) in Concanavalin A as a Tool (Bittiger, H. and Schnebli, H. P., eds.), pp. 17-31, Wiley, London
39 Matsuura, S. and Chen, H. C. (1980) Anal Biochem 106, 402-10
40 McKenzie, G. H., Sawyer, W. H. and Nichol, L. W. (1972) Biochim Biophys Acta 263, 283-93
41 Dawson, R. M. C., Elliott, D. C., Elliott, W. H. and Jones, K. M. (1986) Data for Biochemical Research, Clarendon Press, Oxford
42 Northcote, D. H. (1965) in Methods in Carbohydrate Chemistry, vol. V. (Whistler, R. L., ed.), pp. 49-53, Academic Press, New York, London
43 Sambrook, J., Maniatis, T. and Fritsch, E. F. (1989) Molecular cloning: a laboratory manual, Cold Spring Harbor Laboratory Press, Cold Spring Harbor, N.Y.
44 Svensson, S., Hammarstrom, S. G. and Kabat, E. A. (1970) Immunochemistry 7, 413-22
45 Kennedy, J. F. and Rosevear, A. (1973) J Chem Soc [Perkin 1] 19, 2041-6
46 Lloyd, K. O. (1976) in Concanavalin A as a Tool (Bittiger, H. and Schnebli, H. P., eds.), pp. 323-331, Wiley, London
47 Horstmann, C., Rudolph, A. and Schmidt, P. (1978) Biochem. Physiol. Pflanzen 173, 311-321
48 West, I. and Goldring, O. (1996) Methods Mol Biol 59, 177-85
49 Laenmli, U. K. (1970) Nature 227, 680-5
50 Dubois, M., Gilles, K. A., Hamilton, J. K., Rebers, P. A. and Smith, F. (1956) Analytical Chemistry 28, 350-356
51 Hodge, J. E. and Hofreiter, B. T. (1962) in Methods in Carbohydrate Chemistry, vol. I (Whistler, R. L., Wolfrom, M. L., BeMiller, J. N. and Shafizadeh, F., eds.), pp. 380-394, Academic Press, New York, London 52 Beutler, H.-O. (1984) in Methods of Enzymatic Analysis, vol. VI (Bergmeyer, H. U., ed.), pp. 2-10, Verlag Chemie, Weinheim, Deerfield Beach—Fla., Basel 53 Keppler, D. and Decker, K. (1984) in Methods of Enzymatic Analysis, vol. VI (Bergmeyer, H. U., ed.), pp. 11-18, Verlag Chemie, Weinheim, Deerfield Beach—Fla., Basel 54 Thatcher, D. R. and Hitchcock, A. (1994) in Mechanisms of Protein Folding (Pain, R. H., ed.), pp. 229-261, IRL Press, Oxford 55 Becker, J. W., Cunningham, B. A., Reeke Jr., G. N., Wang, J. L. and Edelman, G. M. (1976) in Concanavalin A as a Tool (Bittiger, H. and Schnebli, H. P., eds.), pp. 33-54, Wiley, London

The invention claimed is:

1. A method of obtaining recombinant mature Concanavalin A protein expressed in a bacterial host cell comprising the steps of:
    (a) expressing said recombinant Concanavalin A in a bacterial host cell;
    (b) producing a lysate containing said Concanavalin A, wherein said lysate has both a soluble and insoluble fraction wherein said insoluble fraction contains Concanavalin A that has a reduced glycogen content and, if present, any glycogen present in the lysate remains in the soluble fraction; and
    (c) recovering said Concanavalin A.

2. The method as claimed in claim 1, wherein the soluble and insoluble fractions are the result of adding a buffer to the lysate, wherein said buffer has such properties that glycogen originating from the bacterial host cell is soluble in the buffer, whereas said Concanavalin A protein is insoluble in the buffer.

3. The method as claimed in claim 2 wherein other impurities are also soluble in said buffer.

4. The method as claimed in claim 2 wherein said buffer is a low ionic strength buffer (I<0.3) with a pH between 8.5 and 9.5.

5. The method as claimed in claim 4 wherein said buffer further comprises a metal chelating agent.

6. The method as claimed in claim 5 wherein said metal chelating agent is ethylene-diamine-tetra-acetic acid.

7. The method as claimed in claim 2 wherein said buffer further comprises a non-ionic detergent.

8. The method as claimed in claim 7 wherein said non-ionic detergent is Triton X-100.

9. The method as claimed in claim 2 wherein said buffer comprises 2-(cyclohexylamino)-ethanesulphonic acid.

10. The method as claimed in claim 2 wherein said buffer comprises borate.

11. The method as claimed in claim 10 wherein said buffer is 20 mM Borax ($Na_2B_4O_7 \cdot 10H_2O$.)

12. The method as claimed in claim 4 wherein said pH is between 9.05-9.25.

13. The method as claimed in claim 4 wherein I<0.1.

14. The method as claimed in claim 1 further comprising the step of removing any residual glycogen-Concanavalin A complex formed.

15. The method as claimed in claim 1 wherein the bacterial host cell is *Escherichia coli*.

16. The method as claimed in claim 15 wherein said *Escherichia coli* cells are incapable of producing glycogen due to defects or mutations in genes for the biosynthesis of glycogen.

17. The method as claimed in claim 1 wherein said bacterial host cells have been cultured in the absence of an assimilable carbohydrate or carbon source that may be accumulated as glycogen.

18. The method as claimed in claim 17 wherein said bacterial host cells have been cultured in the absence of glucose.

19. A method of using a buffer in which glycogen is soluble, but in which recombinant Conconavalin A is insoluble, in the method of obtaining the recombinant Conconavalin A expressed by a bacterial host cell according to claim 1.

20. The method of claim 1 further comprising denaturing, refolding and recovering said insoluble Concanavalin A to produce a mature active form of Concanavalin A.

* * * * *